US010858662B2

(12) United States Patent
Kim et al.

(10) Patent No.: US 10,858,662 B2
(45) Date of Patent: Dec. 8, 2020

(54) GENOME EDITING WITH SPLIT CAS9 EXPRESSED FROM TWO VECTORS

(71) Applicant: INSTITUTE FOR BASIC SCIENCE, Daejeon (KR)

(72) Inventors: Jin Soo Kim, Seoul (KR); Tae Young Koo, Seoul (KR)

(73) Assignee: INSTITUTE FOR BASIC SCIENCE, Daejeon (KR)

( * ) Notice: Subject to any disclaimer, the term of this patent is extended or adjusted under 35 U.S.C. 154(b) by 376 days.

(21) Appl. No.: 15/527,837

(22) PCT Filed: Nov. 19, 2015

(86) PCT No.: PCT/KR2015/012503
§ 371 (c)(1),
(2) Date: May 18, 2017

(87) PCT Pub. No.: WO2016/080795
PCT Pub. Date: May 26, 2016

(65) Prior Publication Data
US 2017/0349905 A1 Dec. 7, 2017

(30) Foreign Application Priority Data
Nov. 19, 2014 (KR) ........................ 10-2014-0161809

(51) Int. Cl.
*C12N 15/74* (2006.01)
*C12N 15/63* (2006.01)
*C12N 15/11* (2006.01)
*C12N 15/864* (2006.01)
*C12N 15/867* (2006.01)
*C12N 9/16* (2006.01)
*C12N 9/22* (2006.01)

(52) U.S. Cl.
CPC ............. *C12N 15/746* (2013.01); *C12N 9/16* (2013.01); *C12N 9/22* (2013.01); *C12N 15/11* (2013.01); *C12N 15/63* (2013.01); *C12N 15/867* (2013.01); *C12N 15/8645* (2013.01)

(58) Field of Classification Search
CPC ................ C12N 15/746; C12N 15/867; C12N 15/8645; C12N 15/11; C12N 9/22; C12N 15/63; C12N 9/16; C12N 2310/10; C12N 15/113
See application file for complete search history.

(56) References Cited

U.S. PATENT DOCUMENTS

2007/0161067 A1 7/2007 Gambhir
2014/0273234 A1 9/2014 Zhang et al.
2014/0295556 A1 10/2014 Joung et al.

FOREIGN PATENT DOCUMENTS

JP 2016-516170 6/2016
JP 2016-538782 12/2016
WO 2013/142578 9/2013
WO 2014-089290 6/2014
WO 2014/191521 12/2014
WO WO 2015/089427 * 6/2015

OTHER PUBLICATIONS

Xiao-Jie et al., J. Med. Genet. 52:289-296, 2015.*
Phillips, A., J. Pharm. Pharmacology 53:1169-1174, 2001.*
Gardlik et al., Med. Sci. Monit. 11(4):RA110-121, 2005.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Sadowski et al., Current Opinion in Structural Biology 19:357-362, 2009.*
Branden et al., Introduction to Protein Structure, Garland Publishing Inc., New York, p. 247, 1991.*
Hyongbum Kim et al., "A guide to genome engineering with programmable nucleases", Nat Rev Genet, 2014, 15: 321-334, published online Apr. 2, 2014.
Youbong Hyun et al., "Site-directed mutagenesis in *Arabidopsis thaliana* using dividing tissue-targeted RGEN of the CRISPR/Cas system to generate heritable null alleles", Planta (2015) 241:271-284, Published online: Oct. 1, 2014.
P. D. Hsu et al., "Development and Applications of CRISPR-Cas9 for Genome Engineering", Cell, vol. 157, No. 6, Jun. 5, 2014, pp. 1262-1278.
H. Nishimasu et al., "Crystal Structure of Cas9 in Complex with Guide RNA and Target DNA", Cell, vol. 156, No. 5, Feb. 1, 2014, p. 935.
A. V. Wright et al., "Rational design of a split-Cas9 enzyme complex", Proceedings of the National Academy of Sciences, vol. 112, No. 10, Feb. 23, 2015, pp. 2984-2989.
B. Zetsche et al., "A split-Cas9 architecture for inducible genome editing and transcription modulation", Nature Biotechnology, vol. 33, No. 2, Feb. 2, 2015, pp. 139-142.
E. J. Fine ET et al., "Trans-spliced Cas9 allows cleavage of HBB and CCR5 genes in human cells using compact expression cassettes", Scientific Reports, vol. 5, No. 1, Jul. 1, 2015.
C. Schmelas et al., "Split Cas9, Not Hairs—Advancing the Therapeutic Index of CRISPR Technology", Biotechnology Journal, Wiley-VCH Verlag, Weinheim, DE, [Online], Jan. 5, 2018 , p. 1700432.

(Continued)

*Primary Examiner* — Delia M Ramirez
(74) *Attorney, Agent, or Firm* — Lex IP Meister, PLLC

(57) ABSTRACT

The present invention relates to a method for regulating gene expression, comprising introducing into a cell each of a recombinant vector which expresses a first domain comprising N-terminus of a Cas9 protein, and a recombinant vector which expresses a second domain comprising C-terminus of a Cas9 protein, a composition comprising the recombinant vectors, a kit for regulating gene expression, and a method for intracellular production of Cas9 protein. Moreover, the present invention relates to a transformed cell introduced with a viral vector which packages the first domain, and a viral vector which packages the second domain, and to a composition comprising a virus produced therefrom.

8 Claims, 7 Drawing Sheets

Specification includes a Sequence Listing.

(56) References Cited

OTHER PUBLICATIONS

EPO, the Extended European Search Report of EP 15861198.8 dated Aug. 2, 2018.
JPO, Office Action of JP 2017-527208 dated Aug. 21, 2018.
SIPO, Office Action of CN 201580069646.8 dated Mar. 30, 2020.

* cited by examiner

| HPRT | Split-Cas9 | 1st Domain | 2nd Domain | Mock |
|---|---|---|---|---|
| INDEL (%) | 27.10 | 0.04 | 0.03 | 0.04 |

| DMD | Split-Cas9 | 1st Domain | 2nd Domain | Mock |
|---|---|---|---|---|
| INDEL (%) | 23.75 | 0.00 | 0.03 | 0.00 |

| CCR5 | Split-Cas9 | 1st Domain | 2nd Domain | Mock |
|---|---|---|---|---|
| INDEL (%) | 20.27 | 0.03 | 0.01 | 0.02 |

| INDEL (%) | Target | OT1 | OT3 | HBB_48 | HBB_75 |
|---|---|---|---|---|---|
| Split-Cas9 | 10.11307 | 22.097 | 0.0619 | 0.6079 | 0.0375 |
| WT Cas9 | 46.1303 | 89.66 | 19.952 | 1.0588 | 14.357 |
| Domain 1 | 0.378484 | 0.0642 | 0.0024 | 0.5667 | 0.0225 |
| Domain 2 | 0.331381 | 0.0922 | 0.0026 | 0.5609 | 0.0194 |
| RGEN(-) | 0.299536 | 0.0502 | 0.0029 | 0.5701 | 0.0072 |

| Specificity ratio (on-target/off-target) | | | | |
|---|---|---|---|---|
| | OT1 | OT3 | HBB 48 | HBB 75 |
| Split-Cas9 | 0.45767598 | 356.924 | 0.10184 | 16.2097 |
| WT Cas9 | 0.51450171 | 4.49377 | 18.8441 | 0.07376 |
| Split-Cas9/WT Cas9 | 0.88955192 | 79.4264 | 0.0054 | 219.803 |

| INDEL (%) | Target | OT1 | OT3 | HBB_48 | HBB_75 |
|---|---|---|---|---|---|
| Split-Cas9 | 9.908309 | 10.22706 | 0.071096 | 0.028461 | 0.00464 |
| WT cas9 | 14.08247 | 21.75932 | 1.425269 | 0.082473 | 0.532676 |
| 1st Domain | 0.297514 | 0.025918 | 0 | 0.007018 | 0.023818 |
| 2nd Domain | 0.272719 | 0.012307 | 0 | 0.023611 | 0.006136 |
| RGEN (-) | 0.278242 | 0.023762 | 0 | 0.021216 | 0 |

| Specificity ratio (on-target/off-target) | | | | |
|---|---|---|---|---|
| | OT1 | OT3 | HBB_48 | HBB_75 |
| Split-Cas9 | 0.96883 | 139.37 | 348.13 | 2135.3 |
| WT cas9 | 0.64719 | 9.8806 | 170.75 | 26.437 |
| Split-Cas9/WT cas9 | 1.49698 | 14.105 | 2.0388 | 80.768 |

| INDEL (%) | MOI 10 | MOI 50 | MOI 100 | Mock |
| --- | --- | --- | --- | --- |
| Day 5 | 0.94 | 4.78 | 4.81 | 0.00 |
| Day 7 | 1.49 | 4.56 | 5.37 | 0.00 |
| Day 10 | 1.35 | 4.99 | 5.26 | 0.00 |

GENOME EDITING WITH SPLIT CAS9 EXPRESSED FROM TWO VECTORS

TECHNICAL FIELD

The present invention relates to a method for regulating gene expression, comprising introducing into a cell each of a recombinant vector which expresses a first domain comprising the N-terminus of Cas9 protein, and a recombinant vector which expresses a second domain comprising the C-terminus of Cas9 protein, a composition comprising the recombinant vectors, a kit for regulating gene expression, and a method for intracellular production of Cas9 protein.

Moreover, the present invention relates to a transformed cell introduced with a viral vector which packages the first domain, and a viral vector which packages the second domain, and to a composition comprising a virus produced therefrom.

BACKGROUND ART

As a tool which is currently being widely used in genetic engineering, restriction enzymes are one of the most important tools in current molecular biology research. However, as the need arose for restriction enzymes which are useful for handling genome-sized DNA and which act as a "rare cutter" capable of recognizing and cleaving a DNA nucleotide sequence having a length of 9 bp or more, various attempts have been made.

As a part of such attempts, artificial nucleases, such as meganuclease, zinc-finger nucleases (ZFNs) and TAL-effector nucleases (TALENs), were developed which are tools capable of inducing mutations of endogenous genes in cells and microorganisms, target gene insertions, and chromosomal rearrangements. These artificial nucleases can be effectively used as a potent and versatile tool in various fields, including the genetic engineering field, the biotechnology field and the medical field. Recent development of RGENs (RNA-guided engineered nucleases), which are third-generation programmable nucleases using the CRISPR/Cas system known as a microbial immune system, has lead to new discovery and innovation in all areas of the biotechnology field (Kim, H. et al., Nat Rev Genet, 2014, 15: 321-334).

The artificial nucleases as described above recognize specific target nucleotide sequences in cells to induce DNA double strand breaks (DSBs). The induced intracellular DSBs can be repaired by the cell's endogenous DNA repair mechanisms (homologous recombination (HR) and nonhomologous end joining (NHEJ)), in which target-specific mutations and genetic modifications occur. When a homologous DNA donor is not present in eukaryotic cells and organisms, the DSBs induced by nucleases can be mainly repaired by the NHEJ mechanism rather than the HR mechanism. HR-mediated mutations occur while the sequence in HR donor DNA is exactly copied, but NHEJ-mediated mutations randomly occur. Because NHEJ is an error-prone repair mechanism, small insertion/deletion mutations (indel mutations) may occur in regions in which DSBs occurred. Such mutations induce frame-shift mutations to cause gene mutations.

In particular, the Cas9 protein of the CRISPR/Cas system is a useful tool in designing genetic modifications in eukaryotic cells and organisms. However, the size of the gene encoding the Cas9 protein is large, and for this reason, when the Cas9 protein is to be inserted into a viral vector for intracellular delivery, there is a problem in that the efficiency of virus production and the efficiency of intracellular delivery are low due to the limited packaging of the viral vector. Thus, there is a need for studies focused on expressing the Cas9 protein by a viral vector.

DISCLOSURE OF INVENTION

Technical Problem

The present inventors have made extensive efforts to overcome the limited packaging of a viral vector and to develop a system capable of expressing the Cas9 protein by a viral vector. As a result, the present inventors have divided the Cas9 protein into two domains which can be packaged into viral vectors, and have constructed recombinant vectors capable of expressing each of the domains. Furthermore, the present inventors have found that, when the recombinant vectors are introduced into a cell, the domains are fused to each other to exhibit Indel (insertion or deletion) effects on genomic target DNA, thereby completing the present invention.

Technical Solution

It is an object of the present invention to provide a method for regulating gene expression, comprising introducing into a cell each of a recombinant vector, which expresses a first domain comprising N-terminus of a Cas9 protein, and a recombinant vector which expresses a second domain comprising C-terminus of a Cas9 protein.

Another object of the present invention is to provide a composition comprising a recombinant vector which expresses a first domain comprising N-terminus of a Cas9 protein, and a recombinant vector which expresses a second domain comprising C-terminus of a Cas9 protein.

Still another object of the present invention is to provide a kit for regulating gene expression, comprising the above-described composition.

Yet another object of the present invention is to provide a transformed cell introduced with a viral vector which packages a first domain comprising N-terminus of a Cas9 protein, and a viral vector which packages a second domain comprising C-terminus of a Cas9 protein.

A further object of the present invention is to provide a composition comprising a culture or cell lysate of the above-described transformed cell.

A still further object of the present invention is to provide a method for intracellular production of Cas9 protein, comprising introducing into a cell each of a recombinant vector, which expresses a first domain comprising N-terminus of a Cas9 protein, and a recombinant vector which expresses a second domain comprising C-terminus of a Cas9 protein.

Advantageous Effects

The present invention could improve the target specificity of Cas9 protein, and also enables to apply the Cas9 protein to the viral vector so that it can be useful for regulation of gene expression using the Cas9 protein.

BRIEF DESCRIPTION OF THE DRAWINGS

FIG. 4 shows the results of next-generation sequencing performed to analyze the efficiency of mutagenesis at an on-target site and off-target sites in Hela cells (FIG. 4*a*) and Hep1 cells (FIG. 4*b*). Specificity was analyzed by the specificity ratio obtained by dividing the efficiency of mutagenesis at the on-target site by the efficiency of mutagenesis at each of four off-target sites.

FIG. 5(*c*) shows the results obtained by co-infecting Hela cells with 10, 50 and 100 MOI (multiplicity of infectivity) of an adeno-associated virus that packages U6 promoter, sgRNA, EFS promoter and a first domain and a virus that packages a second domain, and after 5, 7 and 10 days, analyzing induction of mutation in the DMD exon 51 by next-generation sequencing.

BEST MODE FOR CARRYING OUT THE INVENTION

Figure 1:
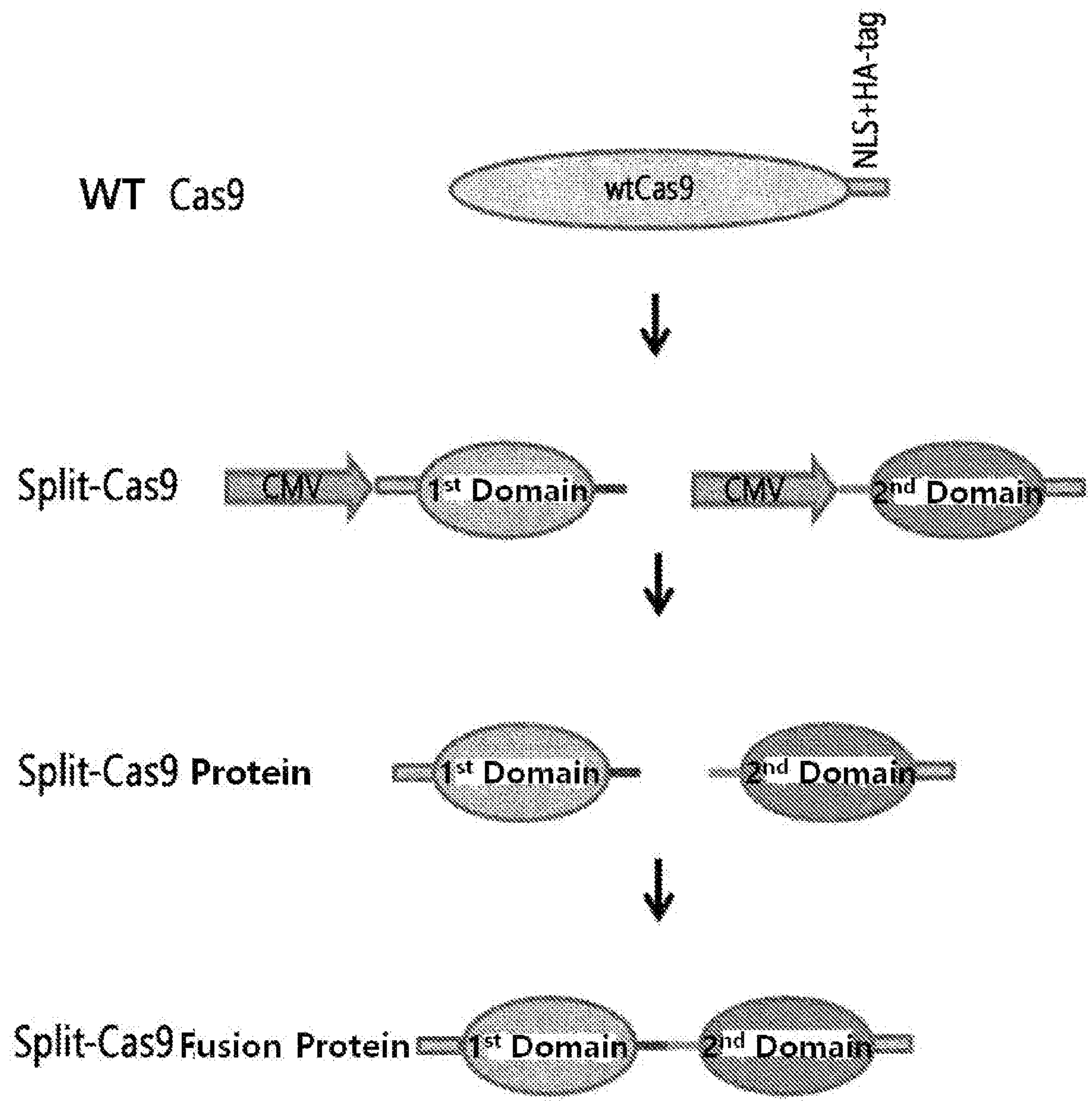
FIG. 1 is a schematic view showing a process in which recombinant vectors comprising the first domain and second domain of the Cas9 protein, respectively, are constructed, and then introduced and expressed in a cell, whereby these domains are fused to each other in the cell to form a full-length Cas9 protein (referred to as Split-Cas9).

To achieve the above objects, one embodiment of the present invention provides a method for regulating gene expression, comprising introducing into a cell each of a recombinant vector, which expresses a first domain comprising N-terminus of a Cas9 protein, and a recombinant vector which expresses a second domain comprising C-terminus of a Cas9 protein.

As used herein, the term "regulating gene expression" refers to all acts to increase or decrease the expression of the gene. In particular, for the purpose of the present invention, the regulation of gene expression may be performed by Cas9 protein. Specifically, any methods of increasing or decreasing the gene expression using Cas9 proteins can be included within the scope of the invention without any limitations. For example, the regulation of gene expression might refer to genome editing, increasing gene expression, or decreasing gene expression.

As used herein, the term "genome editing" refers to a technique capable of introducing a targeted mutation into the nucleotide sequence of a gene in animal and plant cells, including human cells, and refers to knock-out or knock-in a specific gene, or introducing a mutation into a non-coding DNA sequence that does not produce protein. In addition, genome editing enables deletion, duplication, inversion, replacement or rearrangement of genomic DNA.

As used herein, the term "deletion" refers to a mutation caused by deletion of a portion of a chromosome or a portion of DNA nucleotides.

As used herein, the term "duplication" means that two or more identical genes are present in the genome.

As used herein, the term "inversion" means that a portion of the genome is arranged inversely relative to the original genome.

As used herein, the term "replacement" means that one nucleotide sequence is replaced by another nucleotide sequence (that is, replacement of a sequence with information), and does not necessarily mean only that one polynucleotide is chemically or physically replaced by another polynucleotide.

As used herein, the term "rearrangement" refers to a structural change leading to a change in the positions and sequence of a chromosomal gene, and also includes insertion of transposable elements such as transposons. In addition, the term may include the conversion of genetic information by nucleotide rearrangement in DNA molecules.

As used herein, the term "Cas9 protein" refers to the major protein element of the CRISPR/Cas9 system, which forms a complex with crRNA (CRISPR RNA) and tracrRNA (trans-activating crRNA) to form activated endonuclease or nickase.

Cas9 protein or gene information can be obtained from a known database such as the GenBank of NCBI (National Center for Biotechnology Information), but is not limited thereto. For example, the Cas9 protein may be encoded by the nucleotide sequence of SEQ ID NO: 1 or SEQ ID NO: 2, but is not limited thereto, and any Cas9 protein having target-specific nuclease activity together with guide RNA may be included in the scope of the present invention. Furthermore, the Cas9 protein may be bound with a protein transduction domain. The protein transduction domain may be poly-arginine or HIV TAT protein, but is not limited thereto. In addition, those skilled in the art can appreciate that an additional domain can be suitably bound to the Cas9 protein according to the intended use.

In addition, the Cas9 protein may comprise not only wild-type Cas9, but also deactivated Cas9 (dCas9), or Cas9 variants such as Cas9 nickase. The deactivated Cas9 may be RFN (RNA-guided FokI nuclease) comprising a FokI nuclease domain bound to dCas9, or may be dCas9 to which a transcription activator or repressor domain is bound. The Cas9 nickase may be D10A Cas9 or H840A Cas9, but is not limited thereto.

The Cas9 protein of the present invention is not limited in its origin. For example, the Cas9 protein may be derived from *Streptococcus pyogenes, Francisella novicida, Streptococcus thermophilus, Legionella pneumophila, Listeria innocua*, or *Streptococcus mutans*. For the purpose of the invention, the Cas9 protein is one which the size of Cas9 protein is so large that it may not be effectively expressed in the viral vector, but is not limited thereto.

In the present invention, in order to express Cas9 in a viral vector, vectors capable of expressing a portion of Cas9 were constructed. Specifically, the Cas9 protein was divided into domains capable of being expressed from viral vectors, and was expressed from each of the vectors. In the present invention, the first domain and second domain of the Cas9 protein refer to portions of the Cas9 protein, and these domains are expressed from separate vectors to be fused in a cell. In the present invention, the Cas9 protein constructed in this manner was named "split-Cas9" (FIG. 1).

Split-Cas9 of the present invention is characterized in that it is constructed by dividing a conventional Cas9 protein, which is not packaged into a viral vector or the like due to its large size, into domains having a packageable size, and these domains do not lose their function in cells even when these are expressed from the respective vectors.

As used herein, the term "first domain" refers to a domain comprising the N-terminus of the original Cas9 protein, cleaved for the above-described purposes, and the term "second domain" refers to a domain comprising the C-terminus of the original Cas9 protein. In the present invention, the term "first domain" or "second domain" is used interchangeably with the term "half domain". Each of the domains is to be expressed from viral vectors, and thus may have a size ranging from 400 bp to 3.7 kbp, which can be packaged in each viral vector. Specifically, in the present invention, the first domain and the second domain are fused to each other to form the original full-length of Cas9 protein, and thus the entire size of the Cas9 protein minus the size of the other domain would be the size of one domain.

In a specific example of the present invention, a first domain having a size of 2.1 kbp and a second domain having a size of 1.9 kbp were introduced into a plasmid vector and a viral vector. As a result, it was shown that split-Cas9 expressed from the vectors could induce Indel at on-target site in a cell.

Furthermore, those skilled in the art can appreciate that a nucleotide sequence having a specific function may be added to the first domain and the second domain according to the intended use. For example, the first domain and the second domain may further comprise an NLS (nuclear localization signal) sequence, a tag sequence, a splicing donor/splicing acceptor sequence, or the like. Furthermore, the first domain may be encoded by the nucleotide sequence of SEQ ID NO: 3, and the second domain may be encoded by the nucleotide sequence of SEQ ID NO: 5, but the scope of the present invention is not limited thereto.

As used herein, the term "vector" refers to an expression vector capable of expressing a target protein in suitable host cells and to a genetic construct that includes essential regulatory elements to which a gene insert is operably linked in such a manner as to be expressed.

As used herein, the term "operably linked" means that a nucleic acid expression control sequence is functionally linked to a nucleic acid sequence encoding the protein of interest so as to execute general functions. The sequence encoding the first domain or second domain of the nuclease DNA according to the present invention is operably linked to a promoter such that expression of the coding sequence is under the influence or control of the promoter. The two nucleic acid sequences (the sequence encoding the first domain or second domain of DNA and the sequence of the promoter region at the 5' terminus of the encoding sequence) are operably linked to each other when the encoding sequence is transcribed by inducing the promoter action. Furthermore, the linking between the two sequences induces no frame-shift mutation, and the two sequences are operably linked to each other when an expression regulatory sequence does not impair the ability to control expression of each domain. Operable linkage with the recombinant vector can be performed using a gene recombination technique well known in the art, and site-specific DNA cleavage and ligation can be performed using enzymes generally known in the art.

In the present invention, the vector may include an expression regulatory element such as a promoter, an operator, an initiation codon, a stop codon, a polyadenylation signal, or an enhancer, as well as a signal sequence or a reader sequence for membrane targeting and secretion, and may be variously manufactured so as to be adapted for some purpose. The promoter of the vector may be constructive or inductive. Furthermore, the expression vector includes a selective marker for selecting a host cell containing the vector, and a replicable expression vector includes a replication origin. The vector may be self-replicating, or may be integrated into the host DNA. The vector includes a plasmid vector, a cosmid vector, a viral vector, and the like. Specifically, the vector may be the viral vector. An example of the viral vector may include, but is not limited to, a vector derived from Retrovirus, for example, HIV (Human Immunodeficiency Virus), MLV (Murine Leukemia Virus), ASLV (Avian Sarcoma/Leukosis), SNV (Spleen Necrosis Virus), RSV (Rous Sarcoma Virus), MMTV (Mouse Mammary Tumor Virus), Adenovirus, Adeno-associated virus, Herpes simplex virus, etc.

In the present invention, "introducing into a cell" may use any methods known in the art, and a foreign DNA may be introduced into cells by transfection or transduction. The transfection may be performed by various methods known in the art, including calcium phosphate-DNA coprecipitation, DEAE-dextran-mediated transfection, polybrene-mediated transfection, electroporation, microinjection, liposome-mediated transfection, liposome fusion, lipofection and protoplast fusion.

Figure 2:
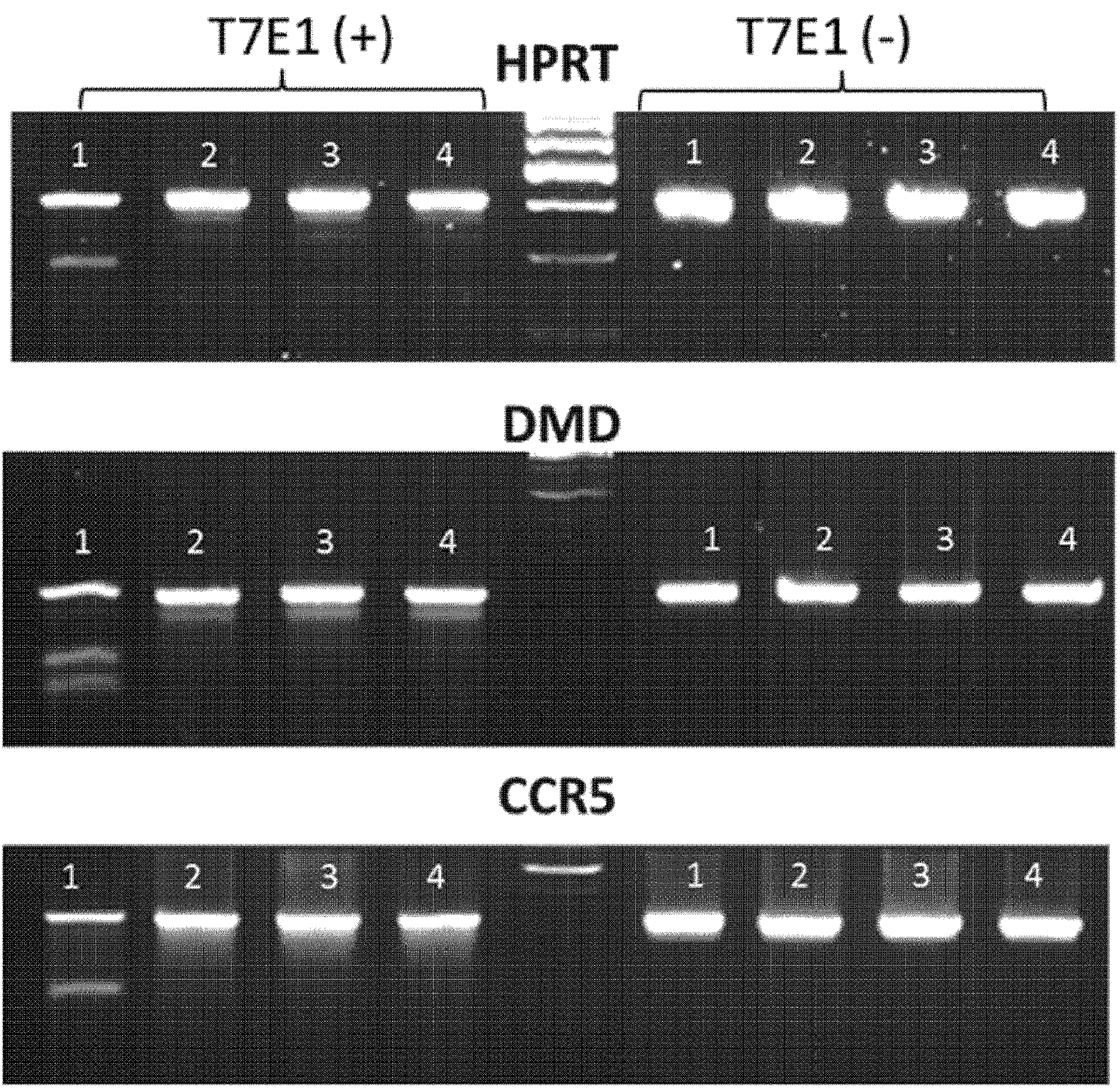
FIG. 2 shows the T7 endonuclease 1 (T7E1) mutation detection assay results indicating that Split-Cas9 protein is formed in a cell and acts together with sgRNA to induce Indel in all of HPRT, DMD and CCR5 genes (1) Split-Cas9+sgRNA, 2) second domain of the Cas9+sgRNA, 3) first domain of the Cas9+sgRNA, 4) mock).
Figure 3:
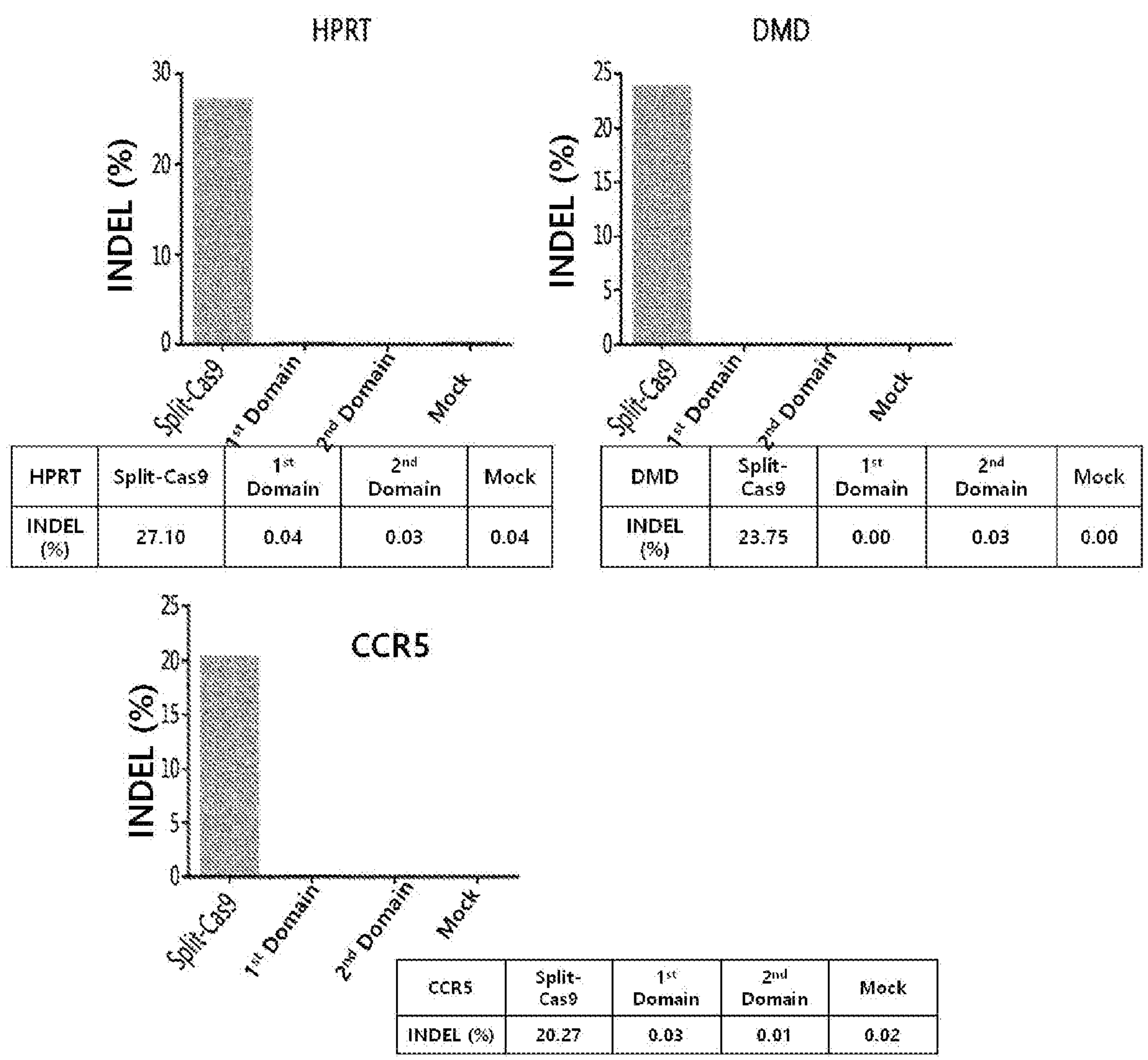
FIG. 3 shows the results of next-generation sequencing performed to analyze the efficiency of mutagenesis of genes target by the Split-Cas9 protein.

In one example of the present invention, each recombinant vector encoding each of the first domain and second domain of the Cas9 protein was constructed (FIG. 1), and then introduced and expressed in a cell. As a result, it was shown that the expressed domains were fused to each other in the cell to function as a full-length Cas9 protein. Specifically, it was shown that the first domain and the second domain, which are half domains, were expressed from the recombinant vectors, and then fused to each other to form a Cas9 form, and the formed Cas9 protein acted together with sgRNA to induce Indel (insertion or deletion) in all target genes (FIGS. 2 and 3).

In another example of the present invention, the target specificities of the split-Cas9 protein in Hela cells and Hep1 cells were examined, and as a result, it was shown that the target specificity of the split-Cas9 protein was 80 to 220-fold higher than the specificity of wild-type Cas9 (FIG. 4). This suggests that when split-Cas9 of the present invention is expressed in a cell, it can act at a desired on-target sites while minimizing off-target effects.

In still another embodiment of the present invention, split-Cas9 was expressed using adeno-associated virus vectors, and cells were infected with the produced virus. As a result, it was shown that split-Cas9 effectively induced Indel (FIG. 5). Accordingly, it was found that the Cas9 protein can also be effectively used through viral vectors comprising split-Cas9.

Specifically, when the vectors are introduced into cells, a sequence-specific guide RNA may additionally be introduced. More specifically, each vector and the guide RNA may be introduced simultaneously, sequentially or in a reversed order.

In the present invention, the "guide RNA" may consist of two RNAs, i.e., crRNA (CRISPR RNA) and tracrRNA (trans-activating crRNA). Alternatively, the guide RNA may be a sgRNA (single-chain RNA) prepared by the fusion of the main parts of crRNA and tracrRNA. In addition, the guide RNA may be a dual RNA comprising a crRNA and a tracrRNA.

RGENs known as third-generation programmable nucleases may be composed of Cas protein and dual RNA or may be composed of Cas protein and sgRNA. The guide RNA may comprise one or more additional nucleotides at the 5' terminus of sgRNA or crRNA of dual RNA, and may be delivered intracellularly as a RNA or a DNA encoding the RNA.

Another embodiment of the present invention provides a composition comprising a recombinant vector which expresses a first domain comprising N-terminus of a Cas9 protein, and a recombinant vector which expresses a second domain comprising C-terminus of a Cas9 protein. The composition may be introduced into cells to regulate expression of a desired gene. The composition may further comprise a sequence-specific guide RNA. The Cas9 protein and the recombinant vector are the same those as described above.

In an example of the present invention, a recombinant vector, which expresses the first domain, and a recombinant vector which expresses the second domain, were introduced into cells. The reason is to deliver the Cas9 protein, which has a size making the Cas9 protein be difficult to package into a vector, and to express the delivered protein more efficiently. The use of a composition comprising each of the recombinant vector enables the Cas9 protein to be more easily expressed in cells. The composition may comprise, in addition to the recombinant vector expressing the first domain and the recombinant vector expressing the second domain, a medium composition capable of maintaining cells or a substance required to introduce the recombinant vectors into cells.

Still another embodiment of the present invention provides a kit for regulating gene expression, comprising a recombinant vector which expresses a first domain of Cas9 protein, and a recombinant vector which expresses a second domain of Cas9 protein. Specifically, the kit may further comprise a sequence-specific guide RNA.

Moreover, the kit according to the present invention may comprise not only a substance that induces or promotes expression of the recombinant vectors or a medium composition capable of maintaining cells, but also a composition capable of facilitating the construction or intracellular introduction of the recombinant vectors and a manual for the construction or intracellular introduction of the recombinant vectors.

Yet another embodiment of the present invention provides a transformed cell, which is introduced with a viral vector packaging a first domain of the Cas9 protein, and a viral vector packaging a second domain of the Cas9 protein.

As used herein, the term "transformed cell" means a cell obtained by introducing a desired polynucleotide into host cells. Transformation may be accomplished by the "introduction" method and can be performed by selecting suitable standard techniques according to host cells, as is known in the art.

It is to be understood that the host cell refers to eukaryotic or prokaryotic cell into which one or more DNAs or vectors are introduced, and refers not only to the particular subject cell but also to the progeny or potential progeny thereof. Because certain modifications may occur in succeeding generations due to either mutation or environmental influences, such progeny may not, in fact, be identical to the parent cell, but are still included within the scope of the term as used herein. In the present invention, the transformed cell is a cell introduced with viral vectors encoding each of the half domains, and a virus that packages the nucleotide sequence encoding each domain of Cas9 can be obtained from the transformed cell. Specifically, the virus can be obtained from a culture or a lysate of the transformed cell.

Examples of the cell include, but are not limited to, prokaryotic cells such as *E. coli*, eukaryotic cells such as yeast, fungi, protozoa, higher plants or insects, mammalian cells such as CHO, HeLa, HEK293 or COS-1, etc.

In addition, the present invention may be applied to all human cells, including somatic cells, germ cells, induced pluripotent stem cells, and adult stem cells.

The somatic cells refer to all cells other than germ cells, which can be obtained from embryos and children and adult bodies, and may also include genetically modified cells derived therefrom. In addition, the adult stem cells may include not only all adult stem cells obtainable from human embryos, neonates and adult bodies, but also extraembryonic stem cells, including cord blood stem cells, placenta stem cells, Wharton's jelly stem cells, amniotic fluid stem cells, and amniotic epithelial cells, as well as genetically modified cells derived therefrom.

In addition, the cells may also be cultured cells (in vitro), graft and primary cultures (in vitro and ex vivo), or in vivo cells, and are not particularly limited as long as they are cells that are generally used in the art.

In another embodiment of the present invention, there is provided a composition comprising a culture or cell lysate of the transformed cell. The transformed cell and the culture and lysate thereof are as described above. The composition comprises a virus that packages the nucleotide sequence encoding each of the domains, and thus may be used to regulate gene expression.

According to the present invention, the limitation in packaging of the Cas9 protein by a vector is overcome, and the efficiency of intracellular delivery of the Cas9 protein is increased by constructing recombinant vectors that individually express the two cleaved domains of the Cas9 protein and delivering the constructed recombinant vectors to be expressed in cells. Thus, the inventive principle developed by the present inventors may be applied regardless of the types of cells or the types of Cas9 protein to increase the efficiency of intracellular delivery of Cas9 protein to thereby efficiently regulate gene expression.

MODE FOR INVENTION

Hereinafter, the present invention will be described in detail with reference to examples. It will be obvious to a person having ordinary skill in the art that these examples are for illustrative purposes only and are not to be construed to limit the scope of the present invention.

EXAMPLE 1

Construction of Recombinant Vectors Expressing Each of First and Second Domains of Cas9 Protein The middle portion of a disordered linker (SEQ ID NO: 9; agcggccagggc; the sequence encoding SGQG amino acids) present in the middle portion of wild-type (WT) Cas9 (CRISPR associated protein 9) protein (SEQ ID NO: 2) was cleaved, thereby constructing two half domains in which SG amino acids and QG amino acids were linked to the first domain and the second domain, respectively.

Each of the half domains was configured such that independent domain thereof could be induced by a CMV promoter. A stop codon was inserted into the cleaved 3'-end of the first domain by PCR cloning such that expression could be completed, and a start codon was linked to the cleaved 5'-end region of the second domain such that expression could be initiated. A HA tag and a NLS (nuclear localization signal) were sequentially inserted downstream of the start codon in the 5'-end region of the first domain, a NLS region and a HA tag were sequentially inserted between the 3'-end and stop codon of the second domain, such that protein expression could be measured by nuclear localization and the HA antibody.

EXAMPLE 2

Examination of Intracellular Introduction of Recombinant Vectors Expressing Each Half Domain and sgRNA and Knock Out of Target Genes The recombinant vectors expressing each half domain, constructed in Example 1, plasmids expressing sgRNA (single guide RNA) for each of CCR5, HPRT and DMD genes, were delivered into cells by transfection using lipofectamin.

As a target sequence for allele knockout of the CCR5 gene, a conversed sequence commonly present in all humans was used, and the 5'-TGACATCAATTATTATACATCGG-3' sequence (SEQ ID NO: 11) present in CCR5 exon 2 was targeted.

Furthermore, as a target sequence for allele knockout of the HPRT gene, the 5'-GCCCCCCTTGAGCACACAGAGGG-3' sequence (SEQ ID NO: 12) present in DMD exon 51 was targeted.

In addition, as a target sequence for allele knockout of the DMD gene, the 5'-TCCTACTCAGACTGTTACTCTGG-3' sequence (SEQ ID NO: 13) present in DMD exon 51 was targeted.

Next, genomic DNAs were extracted from the Hela cells, and then the target sequence region in each of the HPRT, DMD and CCR5 genes was amplified by PCR.

Next, whether Indel (insertion or deletion) was induced was analyzed by T7E1 (T7 endonuclease I) mutation detection assay, and the results of agarose gel analysis are shown in FIG. 2. The T7E1 assay was performed according to a known method. In brief, genomic DNAs were isolated using the DNeasy Blood & Tissue Kit (G-DEX IIc Genomic extraction kit) according to the manufacturer's instruction.

As can be seen in FIG. 2, each of the half domains was expressed from the intracellularly introduced recombinant vectors (constructed in Example 1), and then the expressed half domains were fused to each other to form Cas9 protein (named "Split-Cas9") which then acted together with sgRNA to induce Indel in all the HPRT, DMD and CCR5 genes.

EXAMPLE 3

Analysis of Knockout Efficiency of Target Genes by Split-Cas9 and Target Gene-Specific sgRNA In order to analyze the knockout efficiency of target genes, target sequence regions were amplified by PCR, and then the target sequences were analyzed by a next-generation assay. The results of the analysis indicated that the Indel frequency was 27.1% in the HPRT gene, 23.75% in the DMD gene, and 20.27% in the CCR5 gene. In a control group, only one half domain for the first or second domain was introduced and expressed in cells, and in this case, no Indel appeared (FIG. 3).

From the results as described above, it could be seen that, when the recombinant vectors expressing each half domain of Cas9 were introduced into cells, the half domains were expressed normally and then fused to each other to form a full-length Cas9 protein, indicating that the half domains can act together with sgRNA to exhibit Indel effects on target genes. Cas9 has reduced intracellular delivery efficiency due to the size of a Cas9 expression cassette, which is larger than a size capable of being packaged in a viral vector. According to the present invention, the first and second domains of Cas9 are introduced individually into cells so that they can be expressed in the cells and then fused to each other to exhibit their function, thereby solving the problem associated with the packaging of the Cas9 protein into a vector.

EXAMPLE 4

Analysis of Target Sequence Cleavage Specificity of Split-Cas9

In order to analyze the off-target effect of target genes, cells were treated with each of split-Cas9 and wild-type Cas9 plasmids, and after 3 days, a similar sequence region having a sequence mismatch with the target sequence of the HBB gene was amplified by PCR. Next, the target sequence was analyzed by a next-generation assay.

Figure 4A:
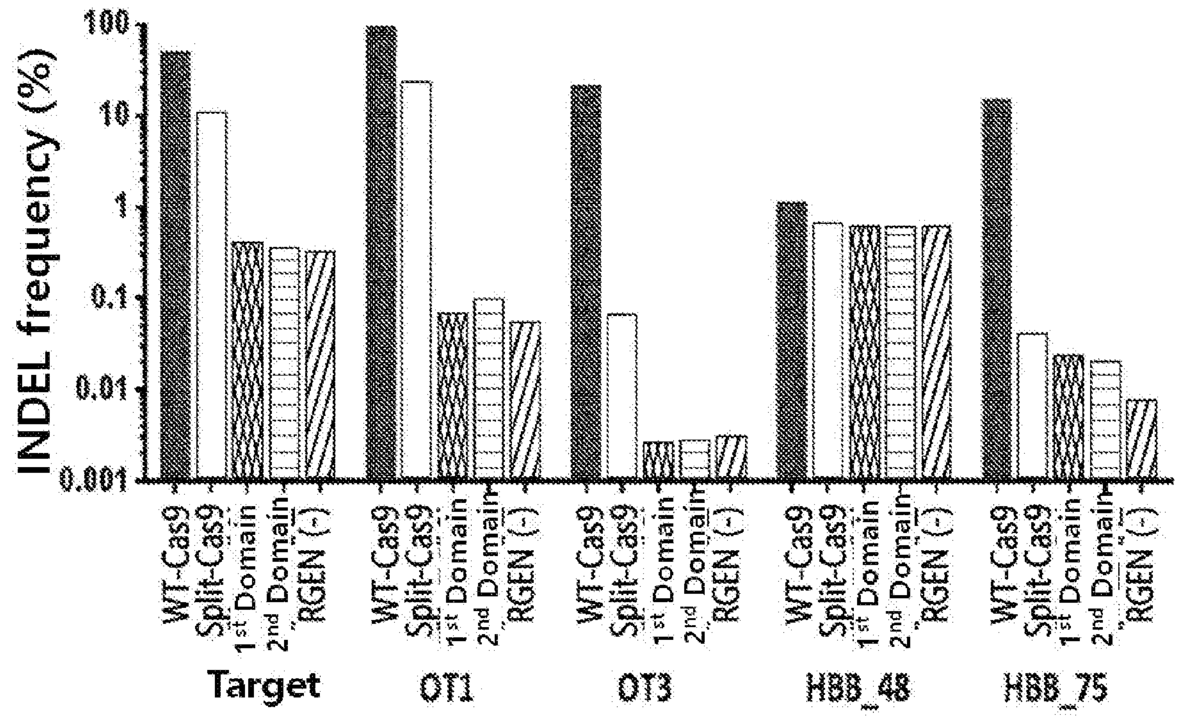
FIG. 4 shows the results of analyzing the specificities of the Split-Cas9 protein for target genes. Specifically.
Figure 4B:
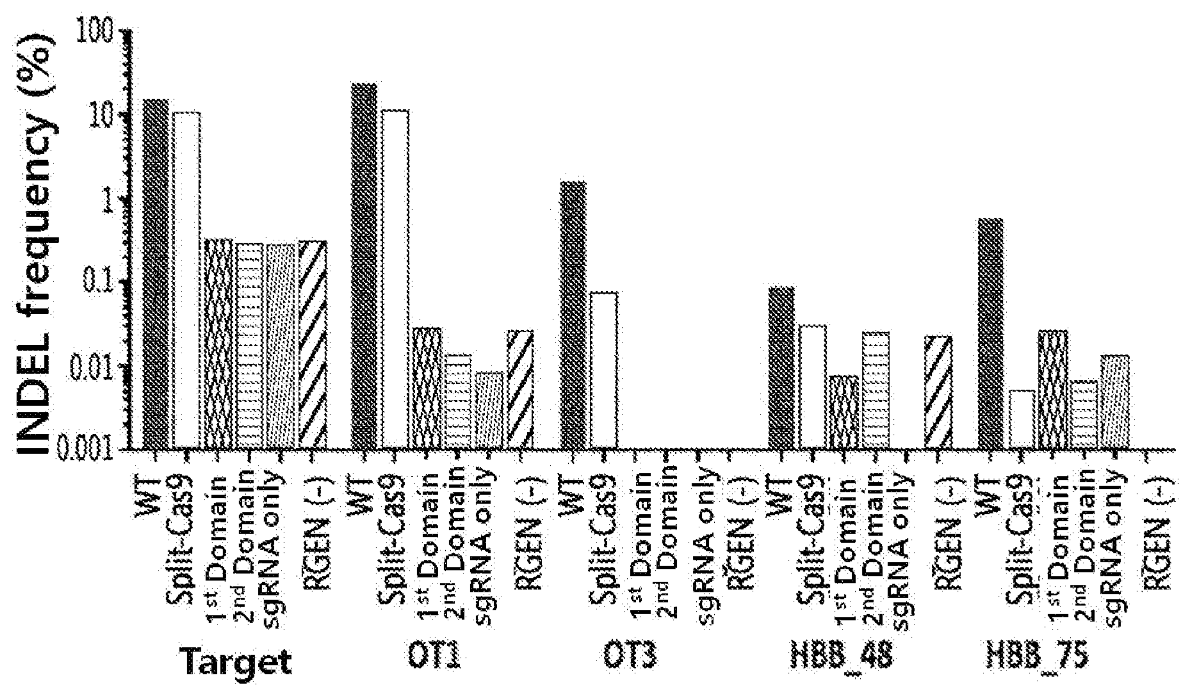

When on-target efficiency in Hela cells was divided by off-target efficiency, it was shown that the specificity of split-Cas9 was up to 220-fold higher than the specificity of wild-type Cas9 (FIG. 4*a*). In addition, it was shown that the specificity of split-Cas9 in Hep1 cells was up to 80-fold higher than the specificity of wild-type Cas9 (FIG. 4*b*).

EXAMPLE 5

Analysis of Target Sequence Cleavage Specificities by Adeno-Associated Virus Expressing Split-Cas9

Figure 5A:
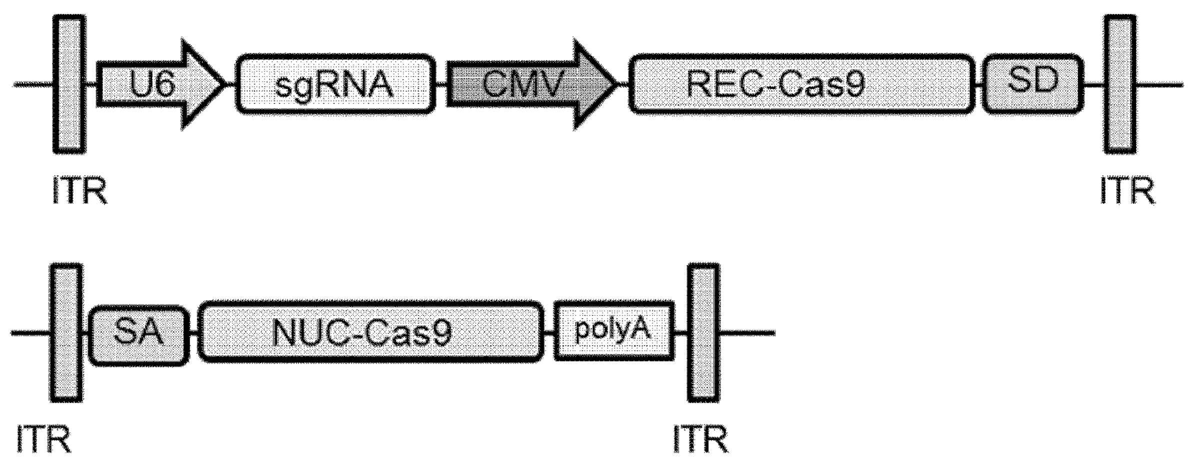
FIG. 5 shows a process of constructing split-Cas9 delivery vectors and the results of examining the function of the vectors. Specifically, FIGS. 5(*a*) and 5(*b*) schematically show construction of adeno-associated virus vectors for delivering split-Cas9. U6 promoter, sgRNA, EFS promoter, a first domain, and a splicing donor were sequentially inserted into an adeno-associated virus vector, thereby constructing a virus vector that packages the first domain. In addition, an adeno-associated virus vector was constructed which includes a splicing acceptor, a second domain or which is capable of packaging the second domain together with U6 promoter and sgRNA.
Figure 5B:
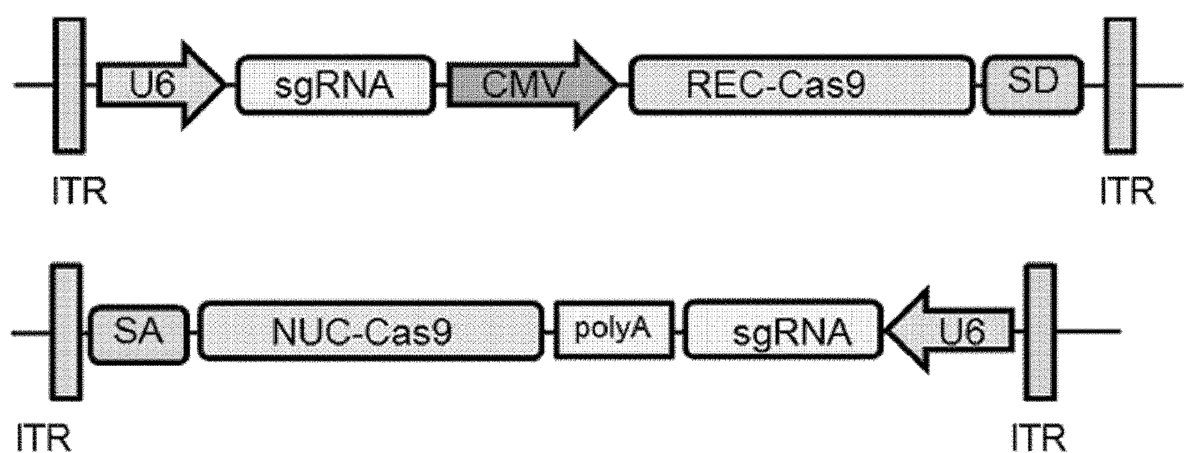

In order to examine whether Split-Cas9 effectively acts even when it is delivered using viral vectors, each of the first and second domains was cloned into adeno-associated virus vector plasmids (FIGS. 5*a* and 5*b*).

A splicing donor was linked to the C-terminal region of the first domain, and a splicing acceptor was linked to the N-terminal region of the second domain. Viruses that package each of the half domains were produced, recovered and delivered intracellularly, and then the cleavage rate of the target sequence region was analyzed.

Figure 5C:
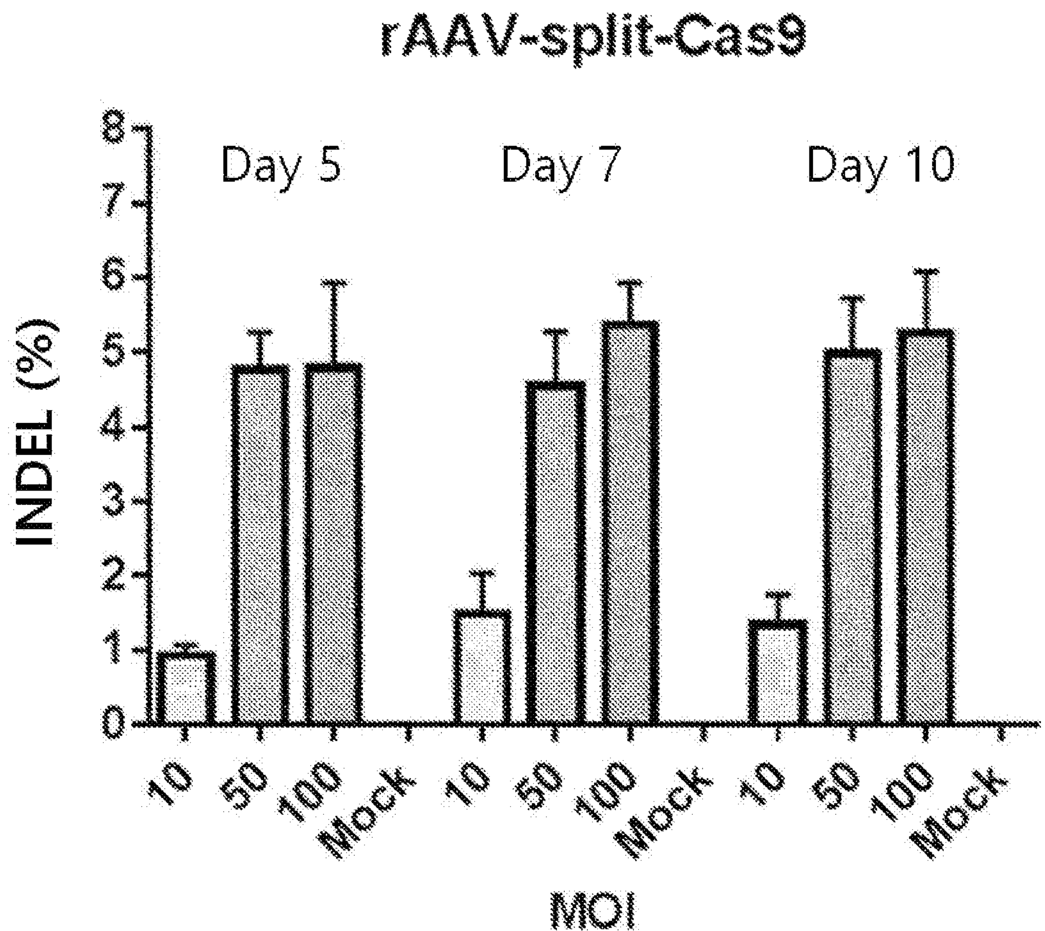

As a result, it could be seen that the half domains were fused to each other to form a full-length Cas9 protein to thereby exhibit gene cleavage effects. Meanwhile, Hela cells were infected with 10, 50 and 100 MOI (multiplicity of infectivity) of adeno-associated virus for delivering Split-Cas9, and after 5, 7 and 10 days, the target sequence cleavage rate was analyzed. As a result, it could be seen that a target sequence cleavage effect of about 5% appeared (FIG. 5*c*). This suggests that split-Cas9 of the present invention effectively acts even when it is delivered using viral vectors.

From the foregoing, it will be understood by those skilled in the art to which the present invention pertains that the present invention can be carried out in other concrete embodiments without changing the technical spirit or essential feature thereof. In this regard, it should be understood that the aforementioned examples are of illustrative in all aspects but not is limited. The scope of the present invention should be construed to include the meaning and scope of the appended claims, and all the alterations and modified forms which are derived from the equivalent concept thereof, rather than the detailed description.

The invention claimed is:

1. A method for introducing a targeted mutation into a genome, comprising introducing into an isolated cell (i) a recombinant vector, which expresses a first domain comprising the N-terminus of a Cas9 protein, and (ii) a recombinant vector which expresses a second domain comprising the C-terminus of a Cas9 protein, wherein the first domain is encoded by the nucleotide sequence of SEQ ID NO: 3, and the second domain is encoded by the nucleotide sequence of SEQ ID NO: 5, wherein the first domain and the second domain are constructed by cleaving a middle portion of the sequence of SEQ ID NO.:10 in the Cas9 protein, in which SG amino acids and QG amino acids are respectively linked to the first domain and the second domain.

2. The method of claim 1, wherein the Cas9 protein is derived from any one selected from the group consisting of *Streptococcus pyogenes, Francisella novicida, Streptococcus thermophilus, Legionella pneumophila, Listeria innocua,* and *Streptococcus mutans.*

3. The method of claim 1, wherein the recombinant vector is a plasmid vector, a cosmid vector, or a viral vector.

4. The method of claim 3, wherein the viral vector is selected from the group consisting of a retrovirus vector, an adenovirus vector, an adeno-associated virus vector, and a herpes simplex virus vector.

5. The method of claim 1, further comprising fusing the first domain and the second domain, which are expressed from each of the introduced recombinant vectors, to form the Cas9 protein.

6. The method of claim 1, wherein the first domain and the second domain each comprises an NLS (nuclear localization signal) sequence, an hemagglutinin (HA) tag sequence, a splicing donor sequence, a splicing acceptor sequence, or a combination thereof.

7. The method of claim 1, wherein a sequence-specific guide RNA is introduced into the cell.

8. The method of claim 7, wherein introducing each vector and the guide RNA is performed in a simultaneous or sequential manner.

* * * * *

SEQUENCE LISTING

<160> NUMBER OF SEQ ID NOS: 54

<210> SEQ ID NO 1
<211> LENGTH: 4104
<212> TYPE: DNA
<213> ORGANISM: Artificial Sequence
<220> FEATURE:
<223> OTHER INFORMATION: Cas9

<400> SEQUENCE: 1

```
atggacaaga agtacagcat cggcctggac atcggtacca acagcgtggg ctgggccgtg     60
atcaccgacg agtacaaggt gcccagcaag aagttcaagg tgctgggcaa caccgaccgc    120
cacagcatca agaagaacct gatcggcgcc ctgctgttcg acagcggcga gaccgccgag    180
gccacccgcc tgaagcgcac cgcccgccgc cgctacaccc gccgcaagaa ccgcatctgc    240
tacctgcagg agatcttcag caacgagatg gccaaggtgg acgacagctt cttccaccgc    300
ctggaggaga gcttcctggt ggaggaggac aagaagcacg agcgccaccc catcttcggc    360
aacatcgtgg acgaggtggc ctaccacgag aagtacccca ccatctacca cctgcgcaag    420
aagctggtgg acagcaccga caaggccgac ctgcgcctga tctacctggc cctggcccac    480
atgatcaagt tccgcggcca cttcctgatc gagggcgacc tgaaccccga caacagcgac    540
gtggacaagc tgttcatcca gctggtgcag acctacaacc agctgttcga ggagaacccc    600
atcaacgcca gcggcgtgga cgccaaggcc atcctgagcg cccgcctgag caagagccgc    660
cgcctggaga acctgatcgc ccagctgccc ggcgagaaga agaacggcct gttcggcaac    720
ctgatcgccc tgagcctggg cctgaccccc aacttcaaga gcaacttcga cctggccgag    780
gacgccaagc tgcagctgag caaggacacc tacgacgacg acctggacaa cctgctggcc    840
cagatcggcg accagtacgc cgacctgttc ctggccgcca agaacctgag cgacgccatc    900
ctgctgagcg acatcctgcg cgtgaacacc gagatcacca aggccccccct gagcgccagc    960
atgatcaagc gctacgacga gcaccaccag gacctgaccc tgctgaaggc cctggtgcgc   1020
cagcagctgc ccgagaagta caaggagatc ttcttcgacc agagcaagaa cggctacgcc   1080
ggctacatcg acggcggcgc cagccaggag gagttctaca agttcatcaa gcccatcctg   1140
gagaagatgg acggcaccga ggagctgctg gtgaagctga accgcgagga cctgctgcgc   1200
aagcagcgca ccttcgacaa cggcagcatc ccccaccaga tccacctggg cgagctgcac   1260
gccatcctgc gccgccagga ggacttctac cccttcctga aggacaaccg cgagaagatc   1320
gagaagatcc tgaccttccg catcccctac tacgtgggcc ccctggcccg cggcaacagc   1380
cgcttcgcct ggatgacccg caagagcgag gagaccatca cccccctggaa cttcgaggag   1440
gtggtggaca agggcgccag cgcccagagc ttcatcgagc gcatgaccaa cttcgacaag   1500
aacctgccca acgagaaggt gctgcccaag cacagcctgc tgtacgagta cttcaccgtg   1560
tacaacgagc tgaccaaggt gaagtacgtg accgagggca tgcgcaagcc cgccttcctg   1620
agcggcgagc agaagaaggc catcgtggac ctgctgttca agaccaaccg caaggtgacc   1680
gtgaagcagc tgaaggagga ctacttcaag aagatcgagt gcttcgacag cgtggagatc   1740
agcggcgtgg aggaccgctt caacgccagc ctgggcacct accacgacct gctgaagatc   1800
atcaaggaca aggacttcct ggacaacgag gagaacgagg acatcctgga ggacatcgtg   1860
ctgaccctga ccctgttcga ggaccgcgag atgatcgagg agcgcctgaa gacctacgcc   1920
cacctgttcg acgacaaggt gatgaagcag ctgaagcgcc gccgctacac cggctggggc   1980
cgcctgagcc gcaagcttat caacggcatc cgcgacaagc agagcggcaa gaccatcctg   2040
```

gacttcctga agagcgacgg cttcgccaac cgcaacttca tgcagctgat ccacgacgac 2100
agcctgacct tcaaggagga catccagaag gcccaggtga gcggccaggg cgacagcctg 2160
cacgagcaca tcgccaacct ggccggcagc cccgccatca agaagggcat cctgcagacc 2220
gtgaaggtgg tggacgagct ggtgaaggtg atgggccgcc acaagcccga gaacatcgtg 2280
atcgagatgg cccgcgagaa ccagaccacc cagaagggcc agaagaacag ccgcgagcgc 2340
atgaagcgca tcgaggaggg catcaaggag ctgggcagcc agatcctgaa ggagcacccc 2400
gtggagaaca cccagctgca gaacgagaag ctgtacctgt actacctgca gaacggccgc 2460
gacatgtacg tggaccagga gctggacatc aaccgcctga gcgactacga cgtggaccac 2520
atcgtgcccc agagcttcct gaaggacgac agcatcgaca acaaggtgct gacccgcagc 2580
gacaagaacc gcggcaagag cgacaacgtg cccagcgagg aggtggtgaa gaagatgaag 2640
aactactggc gccagctgct gaacgccaag ctgatcaccc agcgcaagtt cgacaacctg 2700
accaaggccg agcgcggcgg cctgagcgag ctggacaagg ccggcttcat caagcgccag 2760
ctggtggaga cccgccagat caccaagcac gtggcccaga tcctggacag ccgcatgaac 2820
accaagtacg acgagaacga caagctgatc cgcgaggtga aggtgatcac cctgaagagc 2880
aagctggtga gcgacttccg caaggacttc cagttctaca aggtgcgcga gatcaacaac 2940
taccaccacg cccacgacgc ctacctgaac gccgtggtgg gcaccgccct gatcaagaag 3000
taccccaagc tggagagcga gttcgtgtac ggcgactaca aggtgtacga cgtgcgcaag 3060
atgatcgcca agagcgagca ggagatcggc aaggccaccg ccaagtactt cttctacagc 3120
aacatcatga acttcttcaa gaccgagatc accctggcca acggcgagat ccgcaagcgc 3180
cccctgatcg agaccaacgg cgagaccggc gagatcgtgt gggacaaggg ccgcgacttc 3240
gccaccgtgc gcaaggtgct gagcatgccc caggtgaaca tcgtgaagaa gaccgaggtg 3300
cagaccggcg gcttcagcaa ggagagcatc ctgcccaagc gcaacagcga caagctgatc 3360
gcccgcaaga aggactggga ccccaagaag tacggcggct tcgacagccc caccgtggcc 3420
tacagcgtgc tggtggtggc caaggtggag aagggcaaga gcaagaagct gaagagcgtg 3480
aaggagctgc tgggcatcac catcatggag cgcagcagct tcgagaagaa ccccatcgac 3540
ttcctggagg ccaagggcta caaggaggtg aagaaggacc tgatcatcaa gctgcccaag 3600
tacagcctgt tcgagctgga gaacggccgc aagcgcatgc tggccagcgc cggcgagctg 3660
cagaagggca acgagctggc cctgcccagc aagtacgtga acttcctgta cctggccagc 3720
cactacgaga agctgaaggg cagccccgag gacaacgagc agaagcagct gttcgtggag 3780
cagcacaagc actacctgga cgagatcatc gagcagatca gcgagttcag caagcgcgtg 3840
atcctggccg acgccaacct ggacaaggtg ctgagcgcct acaacaagca ccgcgacaag 3900
cccatccgcg agcaggccga gaacatcatc cacctgttca ccctgaccaa cctgggcgcc 3960
cccgccgcct tcaagtactt cgacaccacc atcgaccgca agcgctacac cagcaccaag 4020
gaggtgctgg acgccaccct gatccaccag agcatcaccg gtctgtacga gacccgcatc 4080
gacctgagcc agctgggcgg cgac 4104

<210> SEQ ID NO 2
<211> LENGTH: 4173
<212> TYPE: DNA
<213> ORGANISM: Artificial Sequence
<220> FEATURE:
<223> OTHER INFORMATION: Cas9-modified

<400> SEQUENCE: 2

```
atggacaaga agtacagcat cggcctggac atcggtacca acagcgtggg ctgggccgtg     60
atcaccgacg agtacaaggt gcccagcaag aagttcaagg tgctgggcaa caccgaccgc    120
cacagcatca agaagaacct gatcggcgcc ctgctgttcg acagcggcga gaccgccgag    180
gccacccgcc tgaagcgcac cgcccgccgc cgctacaccc gccgcaagaa ccgcatctgc    240
tacctgcagg agatcttcag caacgagatg gccaaggtgg acgacagctt cttccaccgc    300
ctggaggaga gcttcctggt ggaggaggac aagaagcacg agcgccaccc catcttcggc    360
aacatcgtgg acgaggtggc ctaccacgag aagtacccca ccatctacca cctgcgcaag    420
aagctggtgg acagcaccga caaggccgac ctgcgcctga tctacctggc cctggcccac    480
atgatcaagt tccgcggcca cttcctgatc gagggcgacc tgaaccccga caacagcgac    540
gtggacaagc tgttcatcca gctggtgcag acctacaacc agctgttcga ggagaacccc    600
atcaacgcca gcggcgtgga cgccaaggcc atcctgagcg cccgcctgag caagagccgc    660
cgcctggaga acctgatcgc ccagctgccc ggcgagaaga agaacggcct gttcggcaac    720
ctgatcgccc tgagcctggg cctgaccccc aacttcaaga gcaacttcga cctggccgag    780
gacgccaagc tgcagctgag caaggacacc tacgacgacg acctggacaa cctgctggcc    840
cagatcggcg accagtacgc cgacctgttc ctggccgcca agaacctgag cgacgccatc    900
ctgctgagcg acatcctgcg cgtgaacacc gagatcacca aggccccct gagcgccagc    960
atgatcaagc gctacgacga gcaccaccag gacctgaccc tgctgaaggc cctggtgcgc   1020
cagcagctgc ccgagaagta caaggagatc ttcttcgacc agagcaagaa cggctacgcc   1080
ggctacatcg acggcggcgc cagccaggag gagttctaca agttcatcaa gcccatcctg   1140
gagaagatgg acggcaccga ggagctgctg gtgaagctga accgcgagga cctgctgcgc   1200
aagcagcgca ccttcgacaa cggcagcatc ccccaccaga tccacctggg cgagctgcac   1260
gccatcctgc gccgccagga ggacttctac cccttcctga aggacaaccg cgagaagatc   1320
gagaagatcc tgaccttccg catcccctac tacgtgggcc ccctggcccg cggcaacagc   1380
cgcttcgcct ggatgacccg caagagcgag gagaccatca ccccctggaa cttcgaggag   1440
gtggtggaca agggcgccag cgcccagagc ttcatcgagc gcatgaccaa cttcgacaag   1500
aacctgccca acgagaaggt gctgcccaag cacagcctgc tgtacgagta cttcaccgtg   1560
tacaacgagc tgaccaaggt gaagtacgtg accgagggca tgcgcaagcc cgccttcctg   1620
agcggcgagc agaagaaggc catcgtggac ctgctgttca agaccaaccg caaggtgacc   1680
gtgaagcagc tgaaggagga ctacttcaag aagatcgagt gcttcgacag cgtggagatc   1740
agcggcgtgg aggaccgctt caacgccagc ctgggcacct accacgacct gctgaagatc   1800
atcaaggaca aggacttcct ggacaacgag gagaacgagg acatcctgga ggacatcgtg   1860
ctgaccctga ccctgttcga ggaccgcgag atgatcgagg agcgcctgaa gacctacgcc   1920
cacctgttcg acgacaaggt gatgaagcag ctgaagcgcc gccgctacac cggctggggc   1980
cgcctgagcc gcaagcttat caacggcatc cgcgacaagc agagcggcaa gaccatcctg   2040
gacttcctga agagcgacgg cttcgccaac cgcaacttca tgcagctgat ccacgacgac   2100
agcctgacct tcaaggagga catccagaag gcccaggtga gcggccaggg cgacagcctg   2160
cacgagcaca tcgccaacct ggccggcagc cccgccatca agaagggcat cctgcagacc   2220
gtgaaggtgg tggacgagct ggtgaaggtg atgggccgcc acaagcccga gaacatcgtg   2280
atcgagatgg cccgcgagaa ccagaccacc cagaagggcc agaagaacag ccgcgagcgc   2340
```

```
atgaagcgca tcgaggaggg catcaaggag ctgggcagcc agatcctgaa ggagcacccc   2400

gtggagaaca cccagctgca gaacgagaag ctgtacctgt actacctgca gaacggccgc   2460

gacatgtacg tggaccagga gctggacatc aaccgcctga gcgactacga cgtggaccac   2520

atcgtgcccc agagcttcct gaaggacgac agcatcgaca acaaggtgct gacccgcagc   2580

gacaagaacc gcggcaagag cgacaacgtg cccagcgagg aggtggtgaa gaagatgaag   2640

aactactggc gccagctgct gaacgccaag ctgatcaccc agcgcaagtt cgacaacctg   2700

accaaggccg agcgcggcgg cctgagcgag ctggacaagg ccggcttcat caagcgccag   2760

ctggtggaga cccgccagat caccaagcac gtggcccaga tcctggacag ccgcatgaac   2820

accaagtacg acgagaacga caagctgatc cgcgaggtga aggtgatcac cctgaagagc   2880

aagctggtga gcgacttccg caaggacttc cagttctaca aggtgcgcga gatcaacaac   2940

taccaccacg cccacgacgc ctacctgaac gccgtggtgg gcaccgccct gatcaagaag   3000

taccccaagc tggagagcga gttcgtgtac ggcgactaca aggtgtacga cgtgcgcaag   3060

atgatcgcca agagcgagca ggagatcggc aaggccaccg ccaagtactt cttctacagc   3120

aacatcatga acttcttcaa gaccgagatc accctggcca acggcgagat ccgcaagcgc   3180

cccctgatcg agaccaacgg cgagaccggc gagatcgtgt gggacaaggg ccgcgacttc   3240

gccaccgtgc gcaaggtgct gagcatgccc caggtgaaca tcgtgaagaa gaccgaggtg   3300

cagaccggcg gcttcagcaa ggagagcatc ctgcccaagc gcaacagcga caagctgatc   3360

gcccgcaaga aggactggga ccccaagaag tacggcggct tcgacagccc caccgtggcc   3420

tacagcgtgc tggtggtggc caaggtggag aagggcaaga gcaagaagct gaagagcgtg   3480

aaggagctgc tgggcatcac catcatggag cgcagcagct tcgagaagaa ccccatcgac   3540

ttcctggagg ccaagggcta caaggaggtg aagaaggacc tgatcatcaa gctgcccaag   3600

tacagcctgt tcgagctgga gaacggccgc aagcgcatgc tggccagcgc cggcgagctg   3660

cagaagggca acgagctggc cctgcccagc aagtacgtga acttcctgta cctggccagc   3720

cactacgaga agctgaaggg cagccccgag gacaacgagc agaagcagct gttcgtggag   3780

cagcacaagc actacctgga cgagatcatc gagcagatca gcgagttcag caagcgcgtg   3840

atcctggccg acgccaacct ggacaaggtg ctgagcgcct acaacaagca ccgcgacaag   3900

cccatccgcg agcaggccga gaacatcatc cacctgttca ccctgaccaa cctgggcgcc   3960

cccgccgcct tcaagtactt cgacaccacc atcgaccgca agcgctacac cagcaccaag   4020

gaggtgctgg acgccaccct gatccaccag agcatcaccg gtctgtacga gacccgcatc   4080

gacctgagcc agctgggcgg cgacggcggc tccggacctc caaagaaaaa gagaaaagta   4140

taccccctacg acgtgcccga ctacgcctaa taa                               4173
```

<210> SEQ ID NO 3
<211> LENGTH: 2145
<212> TYPE: DNA
<213> ORGANISM: Artificial Sequence
<220> FEATURE:
<223> OTHER INFORMATION: domain 1

<400> SEQUENCE: 3

```
atggacaaga agtacagcat cggcctggac atcggtacca acagcgtggg ctgggccgtg     60

atcaccgacg agtacaaggt gcccagcaag aagttcaagg tgctgggcaa caccgaccgc    120

cacagcatca agaagaacct gatcggcgcc ctgctgttcg acagcggcga gaccgccgag    180
```

```
gccacccgcc tgaagcgcac cgcccgccgc cgctacaccc gccgcaagaa ccgcatctgc    240

tacctgcagg agatcttcag caacgagatg gccaaggtgg acgacagctt cttccaccgc    300

ctggaggaga gcttcctggt ggaggaggac aagaagcacg agcgccaccc catcttcggc    360

aacatcgtgg acgaggtggc ctaccacgag aagtacccca ccatctacca cctgcgcaag    420

aagctggtgg acagcaccga caaggccgac ctgcgcctga tctacctggc cctggcccac    480

atgatcaagt tccgcggcca cttcctgatc gagggcgacc tgaaccccga caacagcgac    540

gtggacaagc tgttcatcca gctggtgcag acctacaacc agctgttcga ggagaacccc    600

atcaacgcca gcggcgtgga cgccaaggcc atcctgagcg cccgcctgag caagagccgc    660

cgcctggaga acctgatcgc ccagctgccc ggcgagaaga agaacggcct gttcggcaac    720

ctgatcgccc tgagcctggg cctgaccccc aacttcaaga gcaacttcga cctggccgag    780

gacgccaagc tgcagctgag caaggacacc tacgacgacg acctggacaa cctgctggcc    840

cagatcggcg accagtacgc cgacctgttc ctggccgcca agaacctgag cgacgccatc    900

ctgctgagcg acatcctgcg cgtgaacacc gagatcacca aggccccccct gagcgccagc   960

atgatcaagc gctacgacga gcaccaccag gacctgaccc tgctgaaggc cctggtgcgc   1020

cagcagctgc ccgagaagta caaggagatc ttcttcgacc agagcaagaa cggctacgcc   1080

ggctacatcg acggcggcgc cagccaggag gagttctaca agttcatcaa gcccatcctg   1140

gagaagatgg acggcaccga ggagctgctg gtgaagctga accgcgagga cctgctgcgc   1200

aagcagcgca ccttcgacaa cggcagcatc ccccaccaga tccacctggg cgagctgcac   1260

gccatcctgc gccgccagga ggacttctac cccttcctga aggacaaccg cgagaagatc   1320

gagaagatcc tgaccttccg catcccctac tacgtgggcc ccctggcccg cggcaacagc   1380

cgcttcgcct ggatgacccg caagagcgag gagaccatca ccccctggaa cttcgaggag   1440

gtggtggaca agggcgccag cgcccagagc ttcatcgagc gcatgaccaa cttcgacaag   1500

aacctgccca acgagaaggt gctgcccaag cacagcctgc tgtacgagta cttcaccgtg   1560

tacaacgagc tgaccaaggt gaagtacgtg accgagggca tgcgcaagcc cgccttcctg   1620

agcggcgagc agaagaaggc catcgtggac ctgctgttca agaccaaccg caaggtgacc   1680

gtgaagcagc tgaaggagga ctacttcaag aagatcgagt gcttcgacag cgtggagatc   1740

agcggcgtgg aggaccgctt caacgccagc ctgggcacct accacgacct gctgaagatc   1800

atcaaggaca aggacttcct ggacaacgag gagaacgagg acatcctgga ggacatcgtg   1860

ctgaccctga ccctgttcga ggaccgcgag atgatcgagg agcgcctgaa gacctacgcc   1920

cacctgttcg acgacaaggt gatgaagcag ctgaagcgcc gccgctacac cggctggggc   1980

cgcctgagcc gcaagcttat caacggcatc cgcgacaagc agagcggcaa gaccatcctg   2040

gacttcctga agagcgacgg cttcgccaac cgcaacttca tgcagctgat ccacgacgac   2100

agcctgacct tcaaggagga catccagaag gcccaggtga gcggc                    2145
```

<210> SEQ ID NO 4
<211> LENGTH: 2238
<212> TYPE: DNA
<213> ORGANISM: Artificial Sequence
<220> FEATURE:
<223> OTHER INFORMATION: domain 1-modified

<400> SEQUENCE: 4

```
atggtgtacc cctacgacgt gcccgactac gccgaattgc ctccaaaaaa gaagagaaag     60

gtagggatcc gaattcccgg ggaaaaaccg gacaagaagt acagcatcgg cctggacatc    120
```

```
ggtaccaaca gcgtgggctg ggccgtgatc accgacgagt acaaggtgcc cagcaagaag    180
ttcaaggtgc tgggcaacac cgaccgccac agcatcaaga agaacctgat cggcgccctg    240
ctgttcgaca gcggcgagac cgccgaggcc acccgcctga agcgcaccgc ccgccgccgc    300
tacacccgcc gcaagaaccg catctgctac ctgcaggaga tcttcagcaa cgagatggcc    360
aaggtggacg acagcttctt ccaccgcctg gaggagagct tcctggtgga ggaggacaag    420
aagcacgagc gccaccccat cttcggcaac atcgtggacg aggtggccta ccacgagaag    480
taccccacca tctaccacct gcgcaagaag ctggtggaca gcaccgacaa ggccgacctg    540
cgcctgatct acctggccct ggcccacatg atcaagttcc gcggccactt cctgatcgag    600
ggcgacctga accccgacaa cagcgacgtg gacaagctgt tcatccagct ggtgcagacc    660
tacaaccagc tgttcgagga gaaccccatc aacgccagcg gcgtggacgc caaggccatc    720
ctgagcgccc gcctgagcaa gagccgccgc ctggagaacc tgatcgccca gctgcccggc    780
gagaagaaga acggcctgtt cggcaacctg atcgccctga gcctgggcct gacccccaac    840
ttcaagagca acttcgacct ggccgaggac gccaagctgc agctgagcaa ggacacctac    900
gacgacgacc tggacaacct gctggcccag atcggcgacc agtacgccga cctgttcctg    960
gccgccaaga acctgagcga cgccatcctg ctgagcgaca tcctgcgcgt gaacaccgag   1020
atcaccaagg ccccccctgag cgccagcatg atcaagcgct acgacgagca ccaccaggac   1080
ctgaccctgc tgaaggccct ggtgcgccag cagctgcccg agaagtacaa ggagatcttc   1140
ttcgaccaga gcaagaacgg ctacgccggc tacatcgacg gcggcgccag ccaggaggag   1200
ttctacaagt tcatcaagcc catcctggag aagatggacg gcaccgagga gctgctggtg   1260
aagctgaacc gcgaggacct gctgcgcaag cagcgcacct tcgacaacgg cagcatcccc   1320
caccagatcc acctgggcga gctgcacgcc atcctgcgcc gccaggagga cttctacccc   1380
ttcctgaagg acaaccgcga gaagatcgag aagatcctga ccttccgcat cccctactac   1440
gtgggccccc tggcccgcgg caacagccgc ttcgcctgga tgacccgcaa gagcgaggag   1500
accatcaccc cctggaactt cgaggaggtg gtggacaagg gcgccagcgc ccagagcttc   1560
atcgagcgca tgaccaactt cgacaagaac ctgcccaacg agaaggtgct gcccaagcac   1620
agcctgctgt acgagtactt caccgtgtac aacgagctga ccaaggtgaa gtacgtgacc   1680
gagggcatgc gcaagcccgc cttcctgagc ggcgagcaga agaaggccat cgtggacctg   1740
ctgttcaaga ccaaccgcaa ggtgaccgtg aagcagctga aggaggacta cttcaagaag   1800
atcgagtgct tcgacagcgt ggagatcagc ggcgtggagg accgcttcaa cgccagcctg   1860
ggcacctacc acgacctgct gaagatcatc aaggacaagg acttcctgga caacgaggag   1920
aacgaggaca tcctggagga catcgtgctg accctgaccc tgttcgagga ccgcgagatg   1980
atcgaggagc gcctgaagac ctacgcccac ctgttcgacg acaaggtgat gaagcagctg   2040
aagcgccgcc gctacaccgg ctggggccgc ctgagccgca agcttatcaa cggcatccgc   2100
gacaagcaga gcggcaagac catcctggac ttcctgaaga gcgacggctt cgccaaccgc   2160
aacttcatgc agctgatcca cgacgacagc ctgaccttca aggaggacat ccagaaggcc   2220
caggtgagcg gctaataa                                                 2238
```

```
<210> SEQ ID NO 5
<211> LENGTH: 1959
<212> TYPE: DNA
<213> ORGANISM: Artificial Sequence
<220> FEATURE:
```

<223> OTHER INFORMATION: domain 2

<400> SEQUENCE: 5

```
cagggcgaca gcctgcacga gcacatcgcc aacctggccg gcagccccgc catcaagaag     60
ggcatcctgc agaccgtgaa ggtggtggac gagctggtga aggtgatggg ccgccacaag    120
cccgagaaca tcgtgatcga gatggcccgc gagaaccaga ccacccagaa gggccagaag    180
aacagccgcg agcgcatgaa gcgcatcgag gagggcatca aggagctggg cagccagatc    240
ctgaaggagc accccgtgga gaacacccag ctgcagaacg agaagctgta cctgtactac    300
ctgcagaacg gccgcgacat gtacgtggac caggagctgg acatcaaccg cctgagcgac    360
tacgacgtgg accacatcgt gccccagagc ttcctgaagg acgacagcat cgacaacaag    420
gtgctgaccc gcagcgacaa gaaccgcggc aagagcgaca acgtgcccag cgaggaggtg    480
gtgaagaaga tgaagaacta ctggcgccag ctgctgaacg ccaagctgat cacccagcgc    540
aagttcgaca acctgaccaa ggccgagcgc ggcggcctga gcgagctgga caaggccggc    600
ttcatcaagc gccagctggt ggagacccgc cagatcacca agcacgtggc ccagatcctg    660
gacagccgca tgaacaccaa gtacgacgag aacgacaagc tgatccgcga ggtgaaggtg    720
atcaccctga agagcaagct ggtgagcgac ttccgcaagg acttccagtt ctacaaggtg    780
cgcgagatca acaactacca ccacgcccac gacgcctacc tgaacgccgt ggtgggcacc    840
gccctgatca agaagtaccc caagctggag agcgagttcg tgtacggcga ctacaaggtg    900
tacgacgtgc gcaagatgat cgccaagagc gagcaggaga tcggcaaggc caccgccaag    960
tacttcttct acagcaacat catgaacttc ttcaagaccg agatcaccct ggccaacggc   1020
gagatccgca agcgcccct gatcgagacc aacggcgaga ccggcgagat cgtgtgggac   1080
aagggccgcg acttcgccac cgtgcgcaag gtgctgagca tgccccaggt gaacatcgtg   1140
aagaagaccg aggtgcagac cggcggcttc agcaaggaga gcatcctgcc caagcgcaac   1200
agcgacaagc tgatcgcccg caagaaggac tgggacccca agaagtacgg cggcttcgac   1260
agccccaccg tggcctacag cgtgctggtg gtggccaagg tggagaaggg caagagcaag   1320
aagctgaaga gcgtgaagga gctgctgggc atcaccatca tggagcgcag cagcttcgag   1380
aagaacccca tcgacttcct ggaggccaag ggctacaagg aggtgaagaa ggacctgatc   1440
atcaagctgc ccaagtacag cctgttcgag ctggagaacg gccgcaagcg catgctggcc   1500
agcgccggcg agctgcagaa gggcaacgag ctggccctgc ccagcaagta cgtgaacttc   1560
ctgtacctgg ccagccacta cgagaagctg aagggcagcc ccgaggacaa cgagcagaag   1620
cagctgttcg tggagcagca caagcactac ctggacgaga tcatcgagca gatcagcgag   1680
ttcagcaagc gcgtgatcct ggccgacgcc aacctggaca aggtgctgag cgcctacaac   1740
aagcaccgcg acaagcccat ccgcgagcag gccgagaaca tcatccacct gttcaccctg   1800
accaacctgg gcgcccccgc cgccttcaag tacttcgaca ccaccatcga ccgcaagcgc   1860
tacaccagca ccaaggaggt gctggacgcc accctgatcc accagagcat caccggtctg   1920
tacgagaccc gcatcgacct gagccagctg ggcggcgac                          1959
```

<210> SEQ ID NO 6
<211> LENGTH: 2031
<212> TYPE: DNA
<213> ORGANISM: Artificial Sequence
<220> FEATURE:
<223> OTHER INFORMATION: domain 2-modified

<400> SEQUENCE: 6

```
atgcagggcg acagcctgca cgagcacatc gccaacctgg ccggcagccc cgccatcaag     60
aagggcatcc tgcagaccgt gaaggtggtg gacgagctgg tgaaggtgat gggccgccac    120
aagcccgaga acatcgtgat cgagatggcc cgcgagaacc agaccaccca gaagggccag    180
aagaacagcc gcgagcgcat gaagcgcatc gaggagggca tcaaggagct gggcagccag    240
atcctgaagg agcaccccgt ggagaacacc cagctgcaga acgagaagct gtacctgtac    300
tacctgcaga acggccgcga catgtacgtg gaccaggagc tggacatcaa ccgcctgagc    360
gactacgacg tggaccacat cgtgccccag agcttcctga aggacgacag catcgacaac    420
aaggtgctga cccgcagcga caagaaccgc ggcaagagcg acaacgtgcc cagcgaggag    480
gtggtgaaga agatgaagaa ctactggcgc cagctgctga acgccaagct gatcacccag    540
cgcaagttcg acaacctgac caaggccgag cgcggcggcc tgagcgagct ggacaaggcc    600
ggcttcatca agcgccagct ggtggagacc cgccagatca ccaagcacgt ggcccagatc    660
ctggacagcc gcatgaacac caagtacgac gagaacgaca agctgatccg cgaggtgaag    720
gtgatcaccc tgaagagcaa gctggtgagc gacttccgca aggacttcca gttctacaag    780
gtgcgcgaga tcaacaacta ccaccacgcc cacgacgcct acctgaacgc cgtggtgggc    840
accgccctga tcaagaagta ccccaagctg gagagcgagt tcgtgtacgg cgactacaag    900
gtgtacgacg tgcgcaagat gatcgccaag agcgagcagg agatcggcaa ggccaccgcc    960
aagtacttct tctacagcaa catcatgaac ttcttcaaga ccgagatcac cctggccaac   1020
ggcgagatcc gcaagcgccc cctgatcgag accaacggcg agaccggcga gatcgtgtgg   1080
gacaagggcc gcgacttcgc caccgtgcgc aaggtgctga gcatgcccca ggtgaacatc   1140
gtgaagaaga ccgaggtgca gaccggcggc ttcagcaagg agagcatcct gcccaagcgc   1200
aacagcgaca agctgatcgc ccgcaagaag gactgggacc ccaagaagta cggcggcttc   1260
gacagcccca ccgtggccta cagcgtgctg gtggtggcca aggtggagaa gggcaagagc   1320
aagaagctga agagcgtgaa ggagctgctg ggcatcacca tcatggagcg cagcagcttc   1380
gagaagaacc ccatcgactt cctggaggcc aagggctaca aggaggtgaa gaaggacctg   1440
atcatcaagc tgcccaagta cagcctgttc gagctggaga acggccgcaa gcgcatgctg   1500
gccagcgccg gcgagctgca gaagggcaac gagctggccc tgcccagcaa gtacgtgaac   1560
ttcctgtacc tggccagcca ctacgagaag ctgaagggca gccccgagga caacgagcag   1620
aagcagctgt tcgtggagca gcacaagcac tacctggacg agatcatcga gcagatcagc   1680
gagttcagca agcgcgtgat cctggccgac gccaacctgg acaaggtgct gagcgcctac   1740
aacaagcacc gcgacaagcc catccgcgag caggccgaga acatcatcca cctgttcacc   1800
ctgaccaacc tgggcgcccc cgccgccttc aagtacttcg acaccaccat cgaccgcaag   1860
cgctacacca gcaccaagga ggtgctggac gccaccctga tccaccagag catcaccggt   1920
ctgtacgaga cccgcatcga cctgagccag ctgggcggcg acggcggctc cggacctcca   1980
aagaaaaaga gaaaagtata cccctacgac gtgcccgact acgcctaata a             2031
```

<210> SEQ ID NO 7
<211> LENGTH: 21
<212> TYPE: DNA
<213> ORGANISM: Artificial Sequence
<220> FEATURE:
<223> OTHER INFORMATION: nuclear localization signal

<400> SEQUENCE: 7
ccaaagaaaa agagaaaagt a 21

<210> SEQ ID NO 8
<211> LENGTH: 27
<212> TYPE: DNA
<213> ORGANISM: Artificial Sequence
<220> FEATURE:
<223> OTHER INFORMATION: HA tag

<400> SEQUENCE: 8 taccctacg acgtgcccga ctacgcc 27

<210> SEQ ID NO 9
<211> LENGTH: 12
<212> TYPE: DNA
<213> ORGANISM: Artificial Sequence
<220> FEATURE:
<223> OTHER INFORMATION: linker

<400> SEQUENCE: 9
agcggccagg gc 12

<210> SEQ ID NO 10
<211> LENGTH: 4
<212> TYPE: PRT
<213> ORGANISM: Artificial Sequence
<220> FEATURE:
<223> OTHER INFORMATION: linker

<400> SEQUENCE: 10

Ser Gly Gln Gly
1

<210> SEQ ID NO 11
<211> LENGTH: 23
<212> TYPE: DNA
<213> ORGANISM: Artificial Sequence
<220> FEATURE:
<223> OTHER INFORMATION: CCR5 exon 2 target sequence

<400> SEQUENCE: 11
tgacatcaat tattatacat cgg 23

<210> SEQ ID NO 12
<211> LENGTH: 23
<212> TYPE: DNA
<213> ORGANISM: Artificial Sequence
<220> FEATURE:
<223> OTHER INFORMATION: HPRT exon 3 target sequence

<400> SEQUENCE: 12 gcccccttg agcacacaga ggg 23

<210> SEQ ID NO 13
<211> LENGTH: 23
<212> TYPE: DNA
<213> ORGANISM: Artificial Sequence
<220> FEATURE:
<223> OTHER INFORMATION: DMD exon 51 target sequence

<400> SEQUENCE: 13
tcctactcag actgttactc tgg 23

<210> SEQ ID NO 14
<211> LENGTH: 20
<212> TYPE: DNA

<213> ORGANISM: Artificial Sequence
<220> FEATURE:
<223> OTHER INFORMATION: CCR5 exon 2 target forward primer for T7E1 assay PCR

<400> SEQUENCE: 14
ctccatggtg ctatagagca 20

<210> SEQ ID NO 15
<211> LENGTH: 20
<212> TYPE: DNA
<213> ORGANISM: Artificial Sequence
<220> FEATURE:
<223> OTHER INFORMATION: CCR5 exon 2 target reverse primer for T7E1 assay PCR

<400> SEQUENCE: 15
gccctgtcaa gagttgacac 20

<210> SEQ ID NO 16
<211> LENGTH: 21
<212> TYPE: DNA
<213> ORGANISM: Artificial Sequence
<220> FEATURE:
<223> OTHER INFORMATION: CCR5 exon 2 target forward primer for T7E1 assay nested PCR

<400> SEQUENCE: 16
gagccaagct ctccatctag t 21

<210> SEQ ID NO 17
<211> LENGTH: 20
<212> TYPE: DNA
<213> ORGANISM: Artificial Sequence
<220> FEATURE:
<223> OTHER INFORMATION: CCR5 exon 2 target reverse primer for T7E1 assay nested PCR

<400> SEQUENCE: 17
gccctgtcaa gagttgacac 20

<210> SEQ ID NO 18
<211> LENGTH: 20
<212> TYPE: DNA
<213> ORGANISM: Artificial Sequence
<220> FEATURE:
<223> OTHER INFORMATION: CCR5 exon 2 target forward primer for deep sequencing PCR

<400> SEQUENCE: 18
ctccatggtg ctatagagca 20

<210> SEQ ID NO 19
<211> LENGTH: 20
<212> TYPE: DNA
<213> ORGANISM: Artificial Sequence
<220> FEATURE:
<223> OTHER INFORMATION: CCR5 exon 2 target reverse primer for deep sequencing PCR

<400> SEQUENCE: 19
gccctgtcaa gagttgacac 20

<210> SEQ ID NO 20
<211> LENGTH: 59
<212> TYPE: DNA
<213> ORGANISM: Artificial Sequence
<220> FEATURE:
<223> OTHER INFORMATION: CCR5 exon 2 target forward primer for deep sequencing nested PCR

<400> SEQUENCE: 20
acactctttc cctacacgac gctcttccga tctaagatca ctttttattt atgcacagg 59

<210> SEQ ID NO 21
<211> LENGTH: 54
<212> TYPE: DNA
<213> ORGANISM: Artificial Sequence
<220> FEATURE:
<223> OTHER INFORMATION: CCR5 exon 2 target reverse primer for deep sequencing nested PCR

<400> SEQUENCE: 21
gtgactggag ttcagacgtg tgctcttccg atctatgttg cccacaaaac caaa 54

<210> SEQ ID NO 22
<211> LENGTH: 20
<212> TYPE: DNA
<213> ORGANISM: Artificial Sequence
<220> FEATURE:
<223> OTHER INFORMATION: HPRT exon 3 target forward primer for T7E1 assay PCR

<400> SEQUENCE: 22
ccaggttggt gtggaagttt 20

<210> SEQ ID NO 23
<211> LENGTH: 20
<212> TYPE: DNA
<213> ORGANISM: Artificial Sequence
<220> FEATURE:
<223> OTHER INFORMATION: HPRT exon 3 target reverse primer for T7E1 assay PCR

<400> SEQUENCE: 23
ggacttttga ctccccacaa 20

<210> SEQ ID NO 24
<211> LENGTH: 20
<212> TYPE: DNA
<213> ORGANISM: Artificial Sequence
<220> FEATURE:
<223> OTHER INFORMATION: HPRT exon 3 target forward primer for T7E1 assay nested PCR

<400> SEQUENCE: 24
ccaggttggt gtggaagttt 20

<210> SEQ ID NO 25
<211> LENGTH: 22
<212> TYPE: DNA
<213> ORGANISM: Artificial Sequence
<220> FEATURE:
<223> OTHER INFORMATION: HPRT exon 3 target reverse primer for T7E1 assay nested PCR

<400> SEQUENCE: 25
tggtttgcag agattcaaag aa 22

<210> SEQ ID NO 26
<211> LENGTH: 20
<212> TYPE: DNA
<213> ORGANISM: Artificial Sequence
<220> FEATURE:

<223> OTHER INFORMATION: HPRT exon 3 target forward primer for deep sequencing PCR

<400> SEQUENCE: 26
ccaggttggt gtggaagttt 20

<210> SEQ ID NO 27
<211> LENGTH: 20
<212> TYPE: DNA
<213> ORGANISM: Artificial Sequence
<220> FEATURE:
<223> OTHER INFORMATION: HPRT exon 3 target reverse primer for deep sequencing PCR

<400> SEQUENCE: 27
ggacttttga ctccccacaa 20

<210> SEQ ID NO 28
<211> LENGTH: 53
<212> TYPE: DNA
<213> ORGANISM: Artificial Sequence
<220> FEATURE:
<223> OTHER INFORMATION: HPRT exon 3 target forward primer for deep sequencing nested PCR

<400> SEQUENCE: 28
acactctttc cctacacgac gctcttccga tcttgctcga gatgtgatga agg 53

<210> SEQ ID NO 29
<211> LENGTH: 56
<212> TYPE: DNA
<213> ORGANISM: Artificial Sequence
<220> FEATURE:
<223> OTHER INFORMATION: HPRT exon 3 target reverse primer for deep sequencing nested PCR

<400> SEQUENCE: 29
gtgactggag ttcagacgtg tgctcttccg atctaagaaa acctactgtt gccact 56

<210> SEQ ID NO 30
<211> LENGTH: 25
<212> TYPE: DNA
<213> ORGANISM: Artificial Sequence
<220> FEATURE:
<223> OTHER INFORMATION: DMD exon 51 target forward primer for T7E1 assay PCR

<400> SEQUENCE: 30
acttgtccag gcatgagaat gagca 25

<210> SEQ ID NO 31
<211> LENGTH: 25
<212> TYPE: DNA
<213> ORGANISM: Artificial Sequence
<220> FEATURE:
<223> OTHER INFORMATION: DMD exon 51 target reverse primer for T7E1 assay PCR

<400> SEQUENCE: 31
gctgcgtagt gccaaaacaa acagt 25

<210> SEQ ID NO 32
<211> LENGTH: 25
<212> TYPE: DNA
<213> ORGANISM: Artificial Sequence
<220> FEATURE:
<223> OTHER INFORMATION: DMD exon 51 target forward primer for T7E1 assay nested PCR

<400> SEQUENCE: 32
ccaggcatga gaatgagcaa aatcg 25

<210> SEQ ID NO 33
<211> LENGTH: 24
<212> TYPE: DNA
<213> ORGANISM: Artificial Sequence
<220> FEATURE:
<223> OTHER INFORMATION: DMD exon 51 target reverse primer for T7E1 assay nested PCR

<400> SEQUENCE: 33
ggtaagttct gtccaagccc ggtt 24

<210> SEQ ID NO 34
<211> LENGTH: 25
<212> TYPE: DNA
<213> ORGANISM: Artificial Sequence
<220> FEATURE:
<223> OTHER INFORMATION: DMD exon 51 target forward primer for deep sequencing PCR

<400> SEQUENCE: 34
acttgtccag gcatgagaat gagca 25

<210> SEQ ID NO 35
<211> LENGTH: 25
<212> TYPE: DNA
<213> ORGANISM: Artificial Sequence
<220> FEATURE:
<223> OTHER INFORMATION: DMD exon 51 target reverse primer for deep sequencing PCR

<400> SEQUENCE: 35
gctgcgtagt gccaaaacaa acagt 25

<210> SEQ ID NO 36
<211> LENGTH: 56
<212> TYPE: DNA
<213> ORGANISM: Artificial Sequence
<220> FEATURE:
<223> OTHER INFORMATION: DMD exon 51 target forward primer for deep sequencing nested PCR

<400> SEQUENCE: 36
acactctttc cctacacgac gctcttccga tctggctctt tagcttgtgt ttctaa 56

<210> SEQ ID NO 37
<211> LENGTH: 58
<212> TYPE: DNA
<213> ORGANISM: Artificial Sequence
<220> FEATURE:
<223> OTHER INFORMATION: DMD exon 51 target reverse primer for deep sequencing nested PCR

<400> SEQUENCE: 37
gtgactggag ttcagacgtg tgctcttccg atctggtaag ttctgtccaa gcccggtt 58

<210> SEQ ID NO 38
<211> LENGTH: 57
<212> TYPE: DNA
<213> ORGANISM: Artificial Sequence
<220> FEATURE:
<223> OTHER INFORMATION: On-target (HBB gene) forward primer for deep sequencing nested PCR

<400> SEQUENCE: 38
acactctttc cctacacgac gctcttccga tcttgtcttg taaccttgat accaacc 57

<210> SEQ ID NO 39
<211> LENGTH: 54
<212> TYPE: DNA
<213> ORGANISM: Artificial Sequence
<220> FEATURE:
<223> OTHER INFORMATION: On-target (HBB gene) reverse primer for deep sequencing nested PCR

<400> SEQUENCE: 39
gtgactggag ttcagacgtg tgctcttccg atctgcaacc tcaaacagac acca 54

<210> SEQ ID NO 40
<211> LENGTH: 53
<212> TYPE: DNA
<213> ORGANISM: Artificial Sequence
<220> FEATURE:
<223> OTHER INFORMATION: OT1 target forward primer for deep sequencing nested PCR

<400> SEQUENCE: 40
acactctttc cctacacgac gctcttccga tctgaaaggg gaagatccca gag 53

<210> SEQ ID NO 41
<211> LENGTH: 54
<212> TYPE: DNA
<213> ORGANISM: Artificial Sequence
<220> FEATURE:
<223> OTHER INFORMATION: OT1 target reverse primer for deep sequencing nested PCR

<400> SEQUENCE: 41
gtgactggag ttcagacgtg tgctcttccg atctatttcc aggctatgct tcca 54

<210> SEQ ID NO 42
<211> LENGTH: 53
<212> TYPE: DNA
<213> ORGANISM: Artificial Sequence
<220> FEATURE:
<223> OTHER INFORMATION: OT3 target forward primer for deep sequencing nested PCR

<400> SEQUENCE: 42
acactctttc cctacacgac gctcttccga tcttttgtgt gggatgctga gag 53

<210> SEQ ID NO 43
<211> LENGTH: 56
<212> TYPE: DNA
<213> ORGANISM: Artificial Sequence
<220> FEATURE:
<223> OTHER INFORMATION: OT3 target reverse primer for deep sequencing nested PCR

<400> SEQUENCE: 43
gtgactggag ttcagacgtg tgctcttccg atctagctac cacggtgaca gtaaca 56

<210> SEQ ID NO 44
<211> LENGTH: 53
<212> TYPE: DNA
<213> ORGANISM: Artificial Sequence
<220> FEATURE:
<223> OTHER INFORMATION: HBB_48 target forward primer for deep sequencing nested PCR

<400> SEQUENCE: 44
acactctttc cctacacgac gctcttccga tctaggaggt gagagtccag tcg 53

<210> SEQ ID NO 45
<211> LENGTH: 54
<212> TYPE: DNA
<213> ORGANISM: Artificial Sequence
<220> FEATURE:
<223> OTHER INFORMATION: HBB_48 target reverse primer for deep sequencing nested PCR

<400> SEQUENCE: 45
gtgactggag ttcagacgtg tgctcttccg atctgaacca gctgcctcag actt 54

<210> SEQ ID NO 46
<211> LENGTH: 53
<212> TYPE: DNA
<213> ORGANISM: Artificial Sequence
<220> FEATURE:
<223> OTHER INFORMATION: HBB_75 target forward primer for deep sequencing nested PCR

<400> SEQUENCE: 46
acactctttc cctacacgac gctcttccga tcttgggtgg tagatgagga tga 53

<210> SEQ ID NO 47
<211> LENGTH: 54
<212> TYPE: DNA
<213> ORGANISM: Artificial Sequence
<220> FEATURE:
<223> OTHER INFORMATION: HBB_75 target reverse primer for deep sequencing nested PCR

<400> SEQUENCE: 47
gtgactggag ttcagacgtg tgctcttccg atctcctggc aaaagtgttt ggat 54

<210> SEQ ID NO 48
<211> LENGTH: 23
<212> TYPE: DNA
<213> ORGANISM: Artificial Sequence
<220> FEATURE:
<223> OTHER INFORMATION: On-target sequence (HBB gene)

<400> SEQUENCE: 48
cttgccccac agggcagtaa cgg 23

<210> SEQ ID NO 49
<211> LENGTH: 23
<212> TYPE: DNA
<213> ORGANISM: Artificial Sequence
<220> FEATURE:
<223> OTHER INFORMATION: off-target sequence (OT1)

<400> SEQUENCE: 49
tcagccccac agggcagtaa ggg 23

<210> SEQ ID NO 50
<211> LENGTH: 23
<212> TYPE: DNA
<213> ORGANISM: Artificial Sequence
<220> FEATURE:
<223> OTHER INFORMATION: off-target sequence (OT3)

<400> SEQUENCE: 50
gctgccccac agggcagcaa agg 23

```
<210> SEQ ID NO 51
<211> LENGTH: 23
<212> TYPE: DNA
<213> ORGANISM: Artificial Sequence
<220> FEATURE:
<223> OTHER INFORMATION: off-target sequence (HBB_48)

<400> SEQUENCE: 51

attgccccac ggggcagtga cgg                                              23


<210> SEQ ID NO 52
<211> LENGTH: 23
<212> TYPE: DNA
<213> ORGANISM: Artificial Sequence
<220> FEATURE:
<223> OTHER INFORMATION: off-target sequence (HBB_75)

<400> SEQUENCE: 52

gtggccccac agggcaggaa tgg                                              23


<210> SEQ ID NO 53
<211> LENGTH: 50
<212> TYPE: DNA
<213> ORGANISM: Artificial Sequence
<220> FEATURE:
<223> OTHER INFORMATION: Splicing donor in adeno-associated virus vector
      carrying domain 1 of spCas9

<400> SEQUENCE: 53

gtaagtatca aggttacaag acaggtttaa ggagaccaat agaaactggg                 50


<210> SEQ ID NO 54
<211> LENGTH: 83
<212> TYPE: DNA
<213> ORGANISM: Artificial Sequence
<220> FEATURE:
<223> OTHER INFORMATION: Splicing acceptor in adeno-associated virus
      vector carrying domain 2 of spCas9

<400> SEQUENCE: 54

cttgtcgaga cagagaagac tcttgcgttt ctgataggca cctattggtc ttactgacat      60

ccactttgcc tttctctcca cag                                              83
```